United States Patent
Bornmann et al.

(10) Patent No.: US 6,660,741 B2
(45) Date of Patent: Dec. 9, 2003

(54) ASYMMETRIC SYNTHESIS OF (S,S,R)-(-)-ACTINONIN AND ITS ANALOGS AND USES THEREFOR

(75) Inventors: William G. Bornmann, New York, NY (US); Francis Sirotnak, New York, NY (US); Howard Scher, Tenefly, NJ (US); Ephraim Vidal, Cincinnati, OH (US); Christopher Borella, New York, NY (US); David Scheinberg, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 4 days.

(21) Appl. No.: 10/102,593

(22) Filed: Mar. 19, 2002

(65) Prior Publication Data

US 2002/0198156 A1 Dec. 26, 2002

Related U.S. Application Data

(60) Provisional application No. 60/277,116, filed on Mar. 19, 2001.

(51) Int. Cl.$^7$ .............................................. A61K 31/497
(52) U.S. Cl. .................. 514/254.01; 514/277; 514/315; 514/422; 514/423; 544/372; 546/245; 546/208; 548/471; 548/540; 548/537; 548/533
(58) Field of Search .......................... 514/423, 422, 514/315, 254.01, 277; 548/540, 471, 537, 533; 544/372; 546/208, 245

(56) References Cited

U.S. PATENT DOCUMENTS 4,929,633 A * 5/1990 Shibahara et al. .......... 514/423

5,206,384 A * 4/1993 Shibahara et al. .......... 548/537

* cited by examiner

Primary Examiner—Joseph K. McKane
Assistant Examiner—Robert Shiao
(74) Attorney, Agent, or Firm—Benjamin Aaron Adler

(57) ABSTRACT

The present invention provides methods for the asymmetric synthesis of (S,S,R)-(–)-actinonin and its analogs and the compounds thereby synthesized having a structural formula:

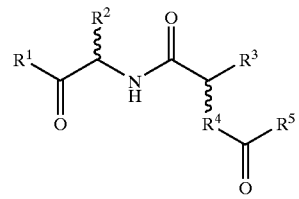

where $R^1$ is an optionally substituted or halogenated alkyl, aryl, heteroalkyl or heteroaryl amine, said $R^1$ further comprising a cyclic or bicyclic structure; $R^2$ is methyl, $CH_2CH_3$, $(CH_2)_2CH_3$, $C(CH_3)_3$, phenyl, 3,4-dichlorophenyl, biphenyl, benzyl, 4-hydroxybenzyl, piperidine, N-Boc-4-piperidine, $CH_2$-(N-Boc-4-piperidine), 4-tetrahydropyran, $CH_2$-4-tetrahydropyran, 3-methyl indolyl, 2-naphthyl, 3-pyridyl, 4-pyridyl, 3-thienyl; $R^3$ is $R^2$ or $C_{3-8}$alkyl, $R^4$ is $C_{1-3}$alkyl; and $R^5$ is $NH_2$, OH, NHOH, NHOCH$_3$, $N(CH_3)OH$, $N(CH_3)OCH_3$, $NHCH_2CH_3$, $NH(CH_2CH_3)$, $NHCH_2(2,4$-$(OCH3)_2Ph$, $NHCH_2(4$-$NO_2)Ph$, $NHN(CH_3)_2$, proline, or 2-hydroxymethyl pyrrolidine. Additionally, a method for the treatment of a neoplastic disease or for the inhibition of tumor cell growth each comprising the step of administering to an individual in need of such treatment a pharmacologically effective dose of the compounds of the present invention are provided.

16 Claims, 7 Drawing Sheets

Scheme 1

Scheme 2

Scheme 4

ASYMMETRIC SYNTHESIS OF (S,S,R)-(-)-ACTINONIN AND ITS ANALOGS AND USES THEREFOR

CROSS-REFERENCE TO RELATED APPLICATIONS

This non-provisional application claims benefit of priority of provisional U.S. Ser. No. 60/277,116, filed Mar. 19, 2001, now abandoned.

BACKGROUND OF THE INVENTION

1. Field of the Invention

The present invention relates generally to the fields of organic chemistry and anti-tumor compounds. More specifically, the present invention relates to the asymmetric synthesis of (S,R.R)-(-)-actinonin and derivatives and analogs thereof and their uses as anti-tumor agents.

2. Description of the Related Art (S,S,R)-(-)-Actinonin (1), was first isolated by Green and Singh from the Malayan strain of Actinomycete, Streptomyces sp. Cutter 12 (N.C.I.B. 8845) (FIG. 1). It has been shown that actinonin exhibits antibiotic and anti-tumor properties (1–7). Studies have demonstrated that actinonin exhibits cytotoxicity towards tumor cell lines in vitro (4). Furthermore, actinonin induces GI arrest and apoptosis in human leukemia and lymphoma cells. It also treats AKR leukemia in AKR mice with minimal toxicity.

Although actinonin is commercially available and usually extracted from Actinomycete and Streptomyces bacteria, specifically *Streptomyces roseopallidus* (9, 10), the yield of compound derived is miniscule. For example, out of a typical ten day culture that yields eleven liters of filtrate, only 146 mg of pure actinonin are isolated. Currently, actinonin is synthesized by either of two synthetic schema. In Ollis' 1975 synthetic method, the synthesis of actinonin is non-stereoselective and the diastereomers have to be separated; difficult process producing small yields (11). Davies' 1992 synthesis is stereoselective and represents the first asymmetric synthesis of (-)-actinonin. An Fe(II)-based chiral auxiliary is used to introduce chirality at the α-position of a carboxylic acid (13,14). However, this process causes disposal problems and therefore commercialization of the synthetic (-)-actinonin is doubtful. It is therefore necessary to develop a method for multi-gram synthesis of actinonin for further testing in various cancer cell lines and for animal studies.

The prior art is deficient in the lack of effective means of asymmetically synthesizing (S,R,R)-(-)-actinonin, its derivatives and its analogs for use as anti-tumor agents. The present invention fulfills this long-standing need and desire in the art.

SUMMARY OF THE INVENTION

One embodiment of the present invention provides a chemical compound comprising an analog or a derivative of (S,S,R)-(-)-actinonin having the structure:

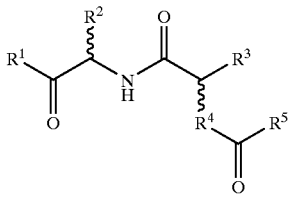

where $R^1$ is an optionally substituted or halogenated alkyl, aryl, heteroalkyl or heteroaryl amine, where $R^1$ further comprises a cyclic or bicyclic structure; $R^2$ is methyl, $CH_2CH_3$, $(CH_2)_2CH_3$, $C(CH_3)_3$, phenyl, 3,4-dichlorophenyl, biphenyl, benzyl, 4-hydroxybenzyl, piperidine, N-Boc-4-piperidine, $CH_2$-(N-Boc-4-piperidine), 4-tetrahydropyran, $CH_2$-4-tetrahydropyran, 3-methyl indolyl, 2-naphthyl, 3-pyridyl, 4-pyridyl, 3-thienyl; $R^3$ is $R^2$ or $C_{3-8}$alkyl, $R^4$ is $C_{1-3}$alkyl; and $R^5$ is $NH_2$, OH, NHOH, $NHOCH_3$, $N(CH_3)OH$, $N(CH_3)OCH_3$, $NHCH_2CH_3$, $NH(CH_2CH_3)$, $NHCH_2(2,4$-$(OCH3)_2Ph$, $NHCH_2(4$-$NO_2)$ Ph, $NHN(CH_3)_2$, proline, or 2-hydroxymethyl pyrrolidine.

Another embodiment of the present invention provides a method for the treatment of a neoplastic disease comprising the step of administering to an individual in need of such treatment a pharmacologically effective dose of (S,S,R)-(-)-actinonin or other chemical compound disclosed herein or a pharmaceutically acceptable salt or hydrate thereof.

Yet another embodiment of the present invention provides a method of inhibiting the growth of a tumor cell comprising the step of contacting said cell with a pharmacologically effective dose of (S,S,R)-(-)-actinonin or other chemical compound disclosed herein or a pharmaceutically acceptable salt or hydrate thereof.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized above may be had by reference to certain embodiments thereof which are illustrated in the appended drawings. These drawings form a part of the specification. It is to be noted; however, that the appended drawings illustrate preferred embodiments of the invention and therefore are not to be considered limiting in their scope.

DETAILED DESCRIPTION OF THE INVENTION

Figure 1A:
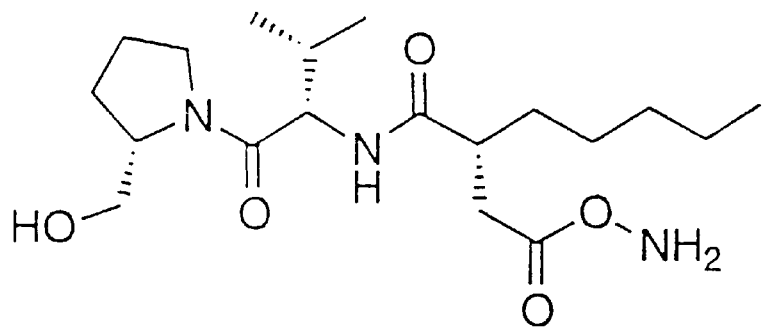
FIG. 1A depicts the structure of (S,S,R)-(-)-actinonin (1).

The following definitions are given for the purpose of facilitating understanding of the inventions disclosed herein.

Any terms not specifically defined should be interpreted according to the common meaning of the term in the art.

As used herein, the term "alkyl" shall refer to optionally substituted straight, branched or cyclic hydrocarbon chains.

As used herein, the term "aryl" shall refer to optionally substituted aromatic mono- or bicyclic hydrocarbons.

As used herein, the term "individual" shall refer to animals and humans.

As used herein, the term "inhibiting" or "inhibition" of the growth of proliferating tumor cells shall include partial or total growth inhibition and also is meant to include decreases in the rate of proliferation or growth of the cells. The biologically inhibitory dose of the composition of the present invention may be determined wo by assessing the effects of the test element on target malignant or abnormally proliferating cell growth in tissue culture, tumor growth in animals and cell culture or any other method known to those of ordinary skill in the art.

The following abbreviations may be used herein: THF: tetrahydrofuran; DMF: dimethylformamide; TFA: trifluoroacetic acid; n-BuLi: n-butyl lithium; OHsuccinNH: hydroxysuccinamide; HOBT: 1-hydroxybenzotriazole; EDC: 1-(3-dimethylaminopropyl)-3-ethylcarbodiimide hydrochloride; DCC: dicyclohexylcarbodiimide; $CH_2Cl_2$: methylene chloride; and TLC: thin layer chromatography.

One embodiment of the present invention provides a chemical compound comprising an analog or a derivative of (S,S,R)-(−)-actinonin having the structure:

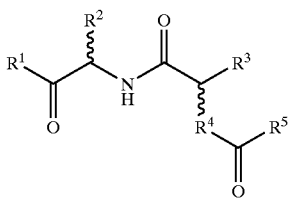

where $R^1$ is an optionally substituted or halogenated alkyl, aryl, heteroalkyl or heteroaryl amine, where $R^1$ further comprises a cyclic or bicyclic structure; $R^2$ is methyl, $CH_2CH_3$, $(CH_2)_2CH_3$, $C(CH_3)_3$, phenyl, 3,4-dichlorophenyl, biphenyl, benzyl, 4-hydroxybenzyl, piperidine, N-Boc-4-piperidine, $CH_2$-(N-Boc-4-piperidine), 4-tetrahydropyran, $CH_2$-4-tetrahydropyran, 3-methyl 4-tetrahydropyran, $CH_2$-4-tetrahydropyran, 3-methyl indolyl, 2-naphthyl, 3-pyridyl, 4-pyridyl, 3-thienyl; $R^3$ is $R^2$ or $C_{3-8}$alkyl, $R^4$ is $C_{1-3}$alkyl; and $R^5$ is $NH_2$, OH, NHOH, $NHOCH_3$, $N(CH_3)OH$, $N(CH_3)OCH_3$, $NHCH_2CH_3$, $NH(CH_2CH_3)$, $NHCH_2(2,4-(OCH3)_2Ph$, $NHCH_2(4-NO_2)$ Ph, $NHN(CH_3)_2$, proline, or 2-hydroxymethyl pyrrolidine.

In one aspect of this embodiment $R^1$ may be those functional groups disclosed in Table 1. Representative examples of the compounds of the present invention are N4-hydroxy-N1-(1-(2-methyl-pyrrolidine-1-carbonyl)-3-methyl-propyl)-2-pentyl-succinamide (27), N4-hydroxy-N1-(1-(2-hydroxymethyl-pyrrolidine-1-carbonyl)-3-methyl-butyl)-2-pentyl-succinamide (35), N4-hydroxy-N1-(1-(2-hydroxymethyl-pyrrolidine-1-carbonyl)-3-methyl-butyl)-2-pentyl succinamide (41), N1-(1-benzyl-2-(2-hydroxymethyl-pyrrolidin-1-yl)-2-oxo-ethyl)-N4-hydroxy-2-pentyl-succinamide (42), N4-hydroxy-N1-(1-(4-hydroxy-benzyl)-2-(2-hydroxymethyl-pyrrolidin-1-yl)-2-oxo-ethyl)-2-pentyl-succinamide (43), N4-hydroxy-N1-(2-(2-hydroxymethyl-pyrrolidin-1-yl)-1(1H-indol-3-yl-methyl)-2-oxo-ethyl)-2-pentyl-succinamide (44), N1-(5-amino-1-(2-hydroxymethyl-pyrrolidine-1-carbonyl)-pentyl)-N4-hydroxy-2pentyl-succinamide (45), N4-hydroxy-N1-(1-(2-hydroxymethyl-piperidine-1-carbonyl)-2-methyl-propyl)-2-pentyl-succinamide (46), N4-hydroxy-N1-(1-(2-hydroxycarbamoyl-pyrrolidine-1-carbonyl)-3-methyl-butyl)-2-pentyl succinamide (47), N4-hydroxy-N1-(1-(2-hydroxymethyl-pyrrolidine-1-carbonyl)-2-methyl-propyl)-2-methyl-succinamide (48), N1-(1-(2-hydroxymethyl-pyrrolidine-1-carbonyl)-3-methyl-butyl)-2-pentyl-succinamide (49), and N1-(1-benzyl-2-(2-hydroxymethyl-pyrrolidin-1-yl)-2-oxo-ethyl)-2-pentyl-succinamide (50), N1-(1-(2-methyl-pyrrolidine-1-carbonyl)-2-methyl-propyl)-2-pentyl-succinamide (51), N4-hydroxy-N1-(1-benzyl-2-(2-methyl-pyrrolidin-1-yl)-2-oxo-ethyl-2-pentyl-succinamide (52), N4-hydroxy-N1-(1-(2-methylamine-pyrrolidine-1-carbonyl)-2-methyl-propyl)-2-pentyl-succinamide (53), 3-[1-(2-hydroxymethyl-pyrrolidin-1-yl)-2-benzylcarbamoyl]-octanoic acid (54), N4-hydroxy-N1-(1-(methyl-2-carboxy-pyrrolidine-1-carbonyl)-2-methyl-propyl)-2-pentyl-succinamide (55), N4-hydroxy-N1-(1-(2-carboxy-pyrrolidine-1-carbonyl)-2-methyl-propyl)-2-pentyl-succinamide (56), N4, N4-diethyl-N1-(1-benzyl-2-(2-hydroxymethyl-pyrrolidin-1-yl)-2-oxo-ethyl-2-pentyl-succinamide (57), N4-ethyl-N1-(1-benzyl-2-(2-hydroxymethyl-pyrrolidin-1-yl)-2-oxo-ethyl-2-pentyl-succinamide (58), N4-(2,4-methoxybenzyl)-N1-(1-benzyl-2-(2-hydroxymethyl-pyrrolidin-1-yl)-2-oxo-ethyl-2-pentyl-succinamide (59), 2-(N', N'-dimethyl-hydrazinocarbonylmethyl)-heptanoic acid [1-benzyl-2-(2-hydroxymethyl-pyrrolidin-1-yl)-2-oxo-ethyl]-amide (60), N4-(4-nitrobenzyl)-N1-(1-benzyl-2-(2-hydroxymethyl-pyrrolidin-1-yl)-2-oxo-ethyl-2-pentyl-succinamide (61), 2-[2-(4-methyl-piperazin-1-yl)-2-oxo-ethyl]-heptanoic acid [1-benzyl-2-(2-hydroxymethyl-pyrrolidin-1-yl)-2-oxo-ethyl]-amide (62), N4-(methoxy)-N1-(1-benzyl-2-(2-hydroxymethyl-pyrrolidin-1-yl)-2-oxo-ethyl -2-pentyl-succinamide (63), N4-(piperidin-1-carbonyl)-N1-(1-benzyl-2-(2-hydroxymethyl-pyrrolidin-1-yl)-2-oxo-ethyl-2-pentyl-succinamide (64), or N4,N4-methoxymethyl-N1-(1-benzyl-2-(2-hydroxymethyl-pyrrolidin-1-yl)-2-oxo-ethyl-2-pentyl-succinamide (65). Pharmaceutical compositions of these compounds are also provided.

In another aspect of this embodiment there is provided a general method of synthesis of (S,S,R)-(−)-actinonin and its analogs and derivatives. This method comprises the steps of forming an optionally O-protected $R^1$-1-carbonyl-C2-($R^2$)-methyleneamine from $R^1$ and an N-protected $R^2$-amino acid 2,5-dioxo-pyrrolidinyl ester and deprotecting said N-protected $R^2$-amino acid with a suitable agent comprising trifluoroacetic acid; forming an $R^3$-carbonyl-oxazolidone from 4-isopropyl-oxazolidin-2-one and $R^3$-carbonyl chloride; treating a solution of 4-(S)-isopropyl-oxazolidin-2-one with a solution of a base comprising n-butyl lithium in hexanes and adding an $R^3$-carbonyl chloride thereby forming an $R^3$-carbonyl oxazolidinone; treating a solution of the $R^3$-carbonyl oxazolidinone sequentially with a base comprising lithium diisopropylamide and with a bromo-$R^4$ acid-tert-butyl ester thereby forming an oxazolidine-$R^3$-carbonyl-$R^4$-acid tert-butyl ester; treating a mixture of the an oxazolidine-$R^3$-carbonyl-$R^4$-acid tert-butyl ester in tetrahydrofuran and water sequentially with hydrogen peroxide in water and with lithium hydroxide in water thereby forming a C2($R^3$)-$R^4$-dicarboxylic acid tert-butyl ester; treating a mixture of the C2($R^3$)-$R^4$-dicarboxylic acid 4-tert-butyl ester and hydroxysuccinimide in a solvent comprising dioxane or dimethylformamide with an imide comprising dicyclohexylcarbodiimide thereby forming an C2($R^3$)-$R^4$-dicarboxylic acid tert-butyl ester-(2,5-dioxo-pyrrolidin-1-yl) ester; treating a solution of the optionally O-protected $R^1$-1-carbonyl-2C($R^2$)-methyleneamine in a solvent comprising tetrahydrofuran sequentially with triethylamine and with the C2($R^3$)-$R^4$-dicarboxylic acid tert-butyl ester-(2,5-dioxo-pyrrolidin-1-yl) ester thereby forming an optionally O-protected $R^1$-1-carbonyl-C2-($R^2$)-carbamoyl-methylene ($R^3$)-$R^4$-carboxylic acid tert-butyl ester; treating a solution of said optionally O-protected $R^1$-1-carbonyl-C2($R^2$)-carbamoyl-methylene($R^3$)-$R^4$-carboxylic acid tert-butyl ester in a solvent comprising methylene chloride with trifluoroacetic acid thereby forming an optionally O-protected $R^1$-1-carbonyl-C2($R^2$)-carbamoyl-methylene ($R^3$)-$R^4$-carboxylic acid; treating the optionally O-protected $R^1$-1-carbonyl-C2-($R^2$)-carbamoyl-methylene($R^3$)-$R^4$-carboxylic acid and hydroxysuccinamide with an imide comprising dicyclohexylcarbodiimide thereby forming a optionally O-protected $R^1$-1-carbonyl-C2($R^2$)-carbamoyl-methylene ($R^3$)-$R^4$-carboxylic acid 2,5-dioxo-pyrrolidin-1-yl ester; treating a suspension of $R^5$ or the chloride thereof, where $R^5$ is optionally O-protected, in a solvent comprising dimethylformamide sequentially with triethylamine and with a solution of the O-protected $R^1$-1-carbonyl-C2($R^2$)-carbamoyl-methylene($R^3$)-$R^4$-carboxylic acid 2,5-dioxo-pyrrolidin-1-yl ester in a solvent comprising dimethylformamide thereby forming an $R^1$-1-carbonyl-C2($R^2$)-carbamoyl-methylene($R^3$)-$R^4$-carbonyl-$R^5$, where $R^1$ and $R^5$ are independently optionally O-protected; and hydrogenating $R^1$ and $R^5$, where $R^1$ and $R^5$ independently comprise an O-protecting group, with hydrogen gas and a catalyst comprising palladium hydroxide in activated carbon where (S,S,R)-(-)-actinonin or a chemical compound disclosed herein is formed.

In an aspect of this embodiment when the $R^1$-$R^5$ substituents are such $R^1$ is 2-hydroxymethyl-pyrrolidine; $R^2$ is benzyl; $R^3$ is pentyl; $R^4$ is methylene; and $R^5$ is NHOCH$_3$, N(CH$_3$)OCH$_3$, NHCH$_2$CH$_3$, NH(CH$_2$CH$_3$)$_2$, NHCH$_2$(2,4-(OCH3)$_2$Ph, NHCH$_2$(4-NO$_2$)Ph, NHN(CH$_3$)$_2$, piperidine or 1-methyl-piperazine an alternate method of synthesis may be used. L-phenylalanine, 2-hydroxymethyl pyrrolidine and $R^5$ are sequentially coupled to 2-pentylsuccinic acid 4-tert-butyl ester 4-(2,5-dioxo-pyrrolidin-1-yl) ester by the method disclosed infra.

In yet another aspect of this embodiment the $R^1$-$R^5$ substituents are such that $R^1$ is 2-hydroxymethyl-pyrrolidine, 2-methylpyrrolidine, 2-methylamine-pyrrolidine, methyl-2-pyrrolidine carboxylate, or 2-hydroxycarbamoyl; $R^2$ is methyl, benzyl, 4-hydroxybenzyl, methylethyl, 2-methyl propyl, 3-methyl-indolyl; $R^3$ is methyl or pentyl; $R^4$ is methylene; and $R^5$ is NH$_2$, OH, NHOH, NHOCH$_3$, N(CH$_3$)OH, N(CH$_3$)OCH$_3$, NHCH$_2$CH$_3$, NH(CH$_2$CH$_3$), NHCH$_2$(2,4-(OCH3)$_2$Ph, NHCH$_2$(4-NO$_2$)Ph, NHN(CH$_3$)$_2$, proline, 2-hydroxymethyl pyrrolidine, piperidine or 1-methyl-piperazine.

In yet another aspect of this embodiment the $R^1$-$R^5$ substituents are such that $R^1$ is 2-methyl pyrrolidine, 2-hydroxymethyl pyrrolidine or 2-hydroxycarbamoyl pyrrolidine; $R^2$ is methyl, CH$_2$CH$_3$, (CH$_2$)$_2$CH$_3$, C(CH$_3$)$_3$; $R^3$ is $R^2$ or C$_{4-7}$alkyleneCH$_3$, $R^4$ is methylene; and $R^5$ is hydroxyamine. The specific synthetic method for this particular aspect is as disclosed infra.

In yet another aspect of this embodiment the $R^1$-$R^5$ substituents are such that $R^1$ is 2-hydroxymethyl pyrrolidine; $R^2$ is methylethyl; $R^3$ is pentyl; $R^4$ is methylene; and $R^5$ is hydroxyamine. (S,S,R)-(-)-actinonin is synthesized in this aspect using the specific method disclosed infra.

The compounds and methods of the present invention may be used to treat neoplastic diseases. Another embodiment of the present invention provides a method for the treatment of a neoplastic disease comprising the step of administering to an individual in need of such treatment a pharmacologically effective dose of (S,S,R)-(-)-actinonin or other chemical compound disclosed herein or a pharmaceutically acceptable salt or hydrate thereof.

Representative examples of preferred compounds used for treatment are N4-hydroxy-N1-(1-(2-hydroxymethyl-pyrrolidine-1-carbonyl)-3-methyl-butyl)-2-pentyl-succinamide 35, N1-(1-(2-methyl-pyrrolidine-1-carbonyl)-2-methyl-propyl)-2-pentyl-succinamide (52), N1-(1-benzyl-2-(2-hydroxymethyl-pyrrolidin-1-yl)-2-oxo-ethyl)-N4-hydroxy-2-pentyl-succinamide (42), N4-hydroxy-N1-(1-(2-hydroxymethyl-pyrrolidine-1-carbonyl)-2-methyl-propyl)-2-methyl-succinamide (48), N4-hydroxy-N1-(1-benzyl-2-(2-methyl-pyrrolidin-1-yl)-2-oxo-ethyl-2-pentyl-succinamide (53) or N4-hydroxy-N1-(1-(methyl-2-carboxy-pyrrolidine-1-carbonyl)-2-methyl-propyl)-2-pentyl-succinamide (56).

Treatment is specifically contemplated in a human. Representative examples of neoplastic diseases include, but are not limited to, human ovarian carcinoma, prostate carcinoma, mammary carcinoma, head and neck squamous cell carcinoma (HNSSC), non-small-cell-lung-cancer adenocarcinoma (NSCLC-AdCa), non-small-cell-lung-cancer squamous cells (NSCLC-SSC), and acute myleg-enous leukemia (AML) cells.

Yet another embodiment of the present invention provides a method of inhibiting the growth of a tumor cell comprising the step of contacting said cell with a pharmacologically effective dose of (S,S,R)-(-)-actinonin or other chemical compound disclosed herein or a pharmaceutically acceptable salt or hydrate thereof. Again representative examples of these compounds and tumor types are those as disclosed supra.

Thus the present invention is directed toward the synthesis and characterization of novel agents that inhibit tumor growth in vitro and in vivo. More specifically, this invention provides for the asymmetric synthesis and effective use of (S,S,R)-(-)-actinonin (1) and its derivatives and analogs as inhibitors of tumor growth in neoplastic diseases. The novel (S,S,R)-actinonin analogs and derivatives of the present invention have the general formula shown below:

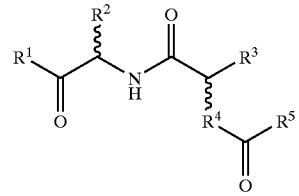

Generally, the compounds are substituted succinamides with $R^4$ as a methylene group although dicarboxylic acids where $R^4$ is either ethylene or propylene may be synthesized. The amide functional group $R^5$ may be mono- or di-substituted with a $C_{1-2}$-alkyl, -alkoxy or phenoxy group (s), preferably $R^5$ is hydroxyamine. $R^2$ and $R^3$ are primarily alkyl although these sidechains may be heterocycles, e.g., piperidinyl, napthyl, pyridyl, or thienyl. Preferably $R^2$ is a branched $C_{2-3}$ alkyl and $R^3$ is pentyl.

In the present invention $R^1$ is an optionally substituted or halogenated alkyl, aryl, heteroalkyl or heteroaryl amine and usually comprises a cyclic or bicyclic structure. $R^1$ may be a mono- or di-substituted simple straight chain or cyclic amine such as methyl, ethyl or benzyl amine or optionally substituted proline, azetidine, aziradine, or hexa- or heptam-ethyleneamime. Generally $R^1$ is a heterocycle optionally substituted in the C2 or C3 positions on the ring. Preferably the heterocycle is pyrrolidine, but may also be pyrrole, indole, indoline, morpholine, piperidine, isoquinoline, or piperazine. Ring substitutions at the C2 or C3 positions can be methyl, ethyl, benzyl, or the heterocylic esters thereof with hydroxymethyl, methyl or hydroxycarbamoyl the preferred substituent on the pyrrolidine ring. Additionally the heterocycles may be substituted with other heterocycles such as pyridinyl, isonicotinyl or furfuryl rings. The heterocycles may be halogenated on any of the available ring positions with a representative example being the fluoroindolines. The substituents disclosed for these $R^1$-$R^5$ groups are not limited to these groups and are not in any way of the invention. Table I details the $R^1$ group substituents for these actinonin analogs.

TABLE 1

R¹ substituents for analogs/derivatives of (S,S,R)-(−)-actinonin

| Compound | alkyl/aryl | ester (carboxylate) | Misc. |
|---|---|---|---|
| pyrrole | | | |
| indole | | | |
| aziradine | | | |
| imidazole | | | |
| proline | | methy | |
| | | ethyl | |
| | | t-butyl | |
| azetidine | 2 or 3-methyl | 2 or 3-methyl | |
| | 2 or 3-ethyl | 2 or 3-ethyl | |
| | | 2 or 3-t-butyl | |
| indoline | | methyl-2 | 2–7 Fl |
| pyrrolidine | 2 or 3-methyl | methyl-2 | 2-NHCH3 |
| | 2 or 3-ethyl | ethyl-2 | 2 or 3-NHOH |
| | 2 or 3-t-butyl | t-butyl-2 | 2-OHcarbamoyl |
| | 2 or 3-phenyl | benzyl-2 | |
| | 2,3-dimethyl | methyl-2-methyl-5 | |
| | 2,4-dimethyl | | |
| | 2,5-dimethyl | | |
| | 2,5-diethyl | | |
| piperidine | 2 or 3-methyl | methyl-2, -3 or -4 | |
| | 2 or 3-ethyl | ethyl-2, -3 or -4 | |
| | | benzyl-2, -3 or -4 | |
| morpholine | | methyl-2 or -3 | |
| | | ethyl-2 or -3 | |
| | | benzyl-2 or -3 | |
| piperazine | 1-benzyl | | 1-furfuryl |
| | | | 1-isonicotinoyl |
| | | | N-tBoc |
| | | | pyridin-2yl-methyl |
| | | | pyridin-3yl-methyl |
| | | | pyridin-4yl-methyl |
| hexamethyleneamine | | methyl-2 or -3 | |
| heptamethyleneamine | | | |
| NH(R) or NRR | methyl | | |
| | ethyl | | |
| | benzyl | | |
| | dimethyl | | |
| | diethyl | | |
| | 2,4-dimethoxy benzyl | | |
| | 4-nitrobenzyl | | |
| 1,4-dioxan-2-yl-methylamine | | | |
| 3,4-dihydro-2H-1,4-benzoxazin-6-ol | | | |
| 6-methoxy-1,2,3,4-tetrahydro-isoquinoline | | | |
| piperazin-1-yl-pyridin-3-yl-methanone | | | |

Figure 1B:
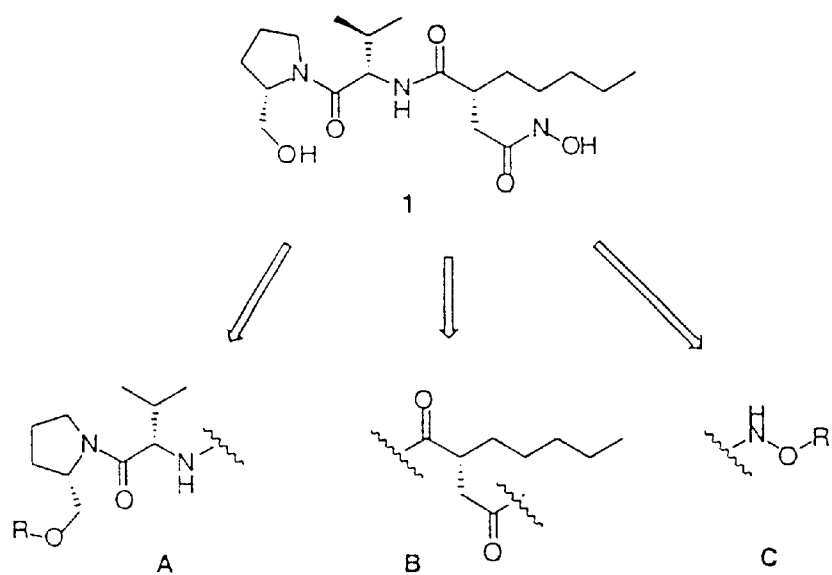
FIG. 1B depicts structurally how (S,S,R)-(-)-actinonin (1) is divided into fragments A, B and C

It should be clear that corresponding actinonin analogs or derivatives readily can be formed using the synthetic methods as provided for (S,S,R)-(−)-actinonin (1) (FIG. 1A) and the analogs or derivatives disclosed herein. The synthetic schema detailed herein provide a scalable process for the asymmetric synthesis of (S,R,R)-(−)-actinonin and its analogs and derivatives. The general structure of these compounds can be divided into three fragments. Fragment A is described as a pseudodipeptide. Fragment B is a succinnic acid or other dicarboxylic acid derivative and is composed of a dicarboxylic acid skeleton functionalized with an $R^3$ group at C2 (or at C3 or C4, depending on the acid) or, alternatively, the α-(or β- or γ-) $R^3$ ester. Fragment C is an optionally suitably protected optionally substituted amine. FIG. 1B depicts these fragments for actinonin.

Figure 1C:
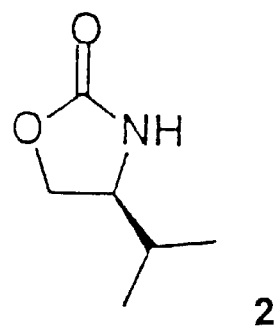
FIG. 1C depicts the structure of Evan's chiral auxiliary (2).

A generalized synthetic scheme to synthesize any of the compounds disclosed herein is shown below. The (−)-actinonin analogs and derivatives are prepared by substituting various amino acids and other reagents to the process. Some substituents would need to be O- or N-protected, e.g., hydroxyl functions on $R^1$ and $R^5$ or the amine in the $R^2$-amino acid in Fragment A. Fragment B may not be commercially available and would have to be synthesized independently. This involves the use of an Evan's chiral auxiliary 2 (13) (FIG. 1C). This chiral auxiliary route provides an easily prepared and inexpensive alternative to the iron (Fe)-based chiral auxiliary. It is contemplated that other structures may be synthesized using the methods disclosed herein.

Fragment A a) An optionally O-protected $R^1$-1-carbonyl-C2-($R^2$)-methyleneamine from $R^1$ and an N-protected $R^2$-amino acid 2,5-dioxo-pyrrolidinyl ester is formed. A suitable agent, e.g. trifluoroacetic acid (TFA) deprotects the N-protected $R^2$-amino.

OH-CO-CH($R^2$)-NH-boc+OhsuccinNH$_2$→succinN-O-CO-CH($R^2$)-NH-boc succinN-O-CO-CH($R^2$)-NH-boc+$R^1$(optionally O-protect) →$R^1$-CO-CH($R^2$)-NH2(A)

Fragment B
b) Forming an $R^3$-carbonyl-oxazolidone from 4-isopropyl-oxazolidin-2-one and $R^3$-carbonyl chloride;
c) Treating a solution of 4-(S)-isopropyl-oxazolidin-2-one with a solution of a base, e.g., n-butyl lithium in hexanes, and adding an $R^3$-carbonyl chloride to form an $R^3$-carbonyl oxazolidinone.
d) Treating a solution of the $R^3$-carbonyl oxazolidinone sequentially with a base, e.g., lithium diisopropylamide, and with a bromo-$R^4$ acid-tert-butyl ester to form an oxazolidine-$R^3$-carbonyl-$R^4$-acid tert-butyl ester.
e) Treating a mixture of the an oxazolidine-$R^3$-carbonyl-$R^4$-acid tert-butyl ester in tetrahydrofuran and water sequentially with hydrogen peroxide in water and with lithium hydroxide in water to form a $C2(R^3)$-$R^4$-dicarboxylic acid tert-butyl ester;
f) Treating a mixture of the $C2(R^3)$-$R^4$-dicarboxylic acid 4-tert-butyl ester and hydroxysuccinimide in a solvent, e.g., dioxane or dimethylformamide, with an imide, e.g., dicyclohexylcarbodiimide to form an $C2(R^3)$-$R^4$-dicarboxylic acid tert-butyl ester-(2,5-dioxo-pyrrolidin-1-yl) ester.

Cl-CO-$R^3$+4-isopropropyl-oxazolidin-2-one→$R^3$-CO-oxazolidone $R^3$-CO-oxazolidone+t-buBrR$^4$ ester→oxaz-CO-CH($R^3$)-CH($R^4$-COO-tb u oxaz-CO-CH($R^3$)-$R^4$-COO-tbu→HO-CO-CH($R^3$)-$R^4$-COO-tb u HO-CO-CH($R^3$)-$R^4$-COO-tbu+OHsuccinNH→succinN-OCOCH($R^3$)-$R^4$-COO-tbu (B)

Fragment A+Fragment B
g) Treating a solution of the optionally O-protected $R^1$-1-carbonyl-2-($R^2$)-methyleneamine in a solvent, e.g., tetrahydrofuran, sequentially with triethylamine and with the $C2(R^3)$-$R^4$-dicarboxylic acid tert-butyl ester-(2,5-dioxo-pyrrolidin-1-yl) ester to form an optionally O-protected $R^1$-1-carbonyl-2-($R^2$)-carbamoyl-methylene($R^3$)-$R^4$-carboxylic acid tert-butyl ester.
h) Treating a solution of the optionally O-protected $R^1$-1-carbonyl-C2($R^2$)-carbamoyl-methylene($R^3$)-$R^4$-carboxylic acid tert-butyl ester in a solvent, e.g., methylene chloride, with TFA to form an optionally O-protected $R^1$-1-carbonyl-C2($R^2$)-carbamoyl-methylene($R^3$)-$R^4$-carboxylic acid.
i) Treating the optionally O-protected $R^1$-1-carbonyl-2C-($R^2$)-carbamoyl-methylene($R^3$)-$R^4$-carboxylic acid and hydroxysuccinamide with an imide, e.g., DCC, to form an optionally O-protected $R^1$-1-carbonyl-C2($R^2$)-carbamoyl-methylene($R^3$)-$R^4$-carboxylic acid 2,5-dioxo-pyrrolidin-1-yl ester.

succinN-OCOCH($R^3$)-$R^4$-COO-tbu+$R^1$-CO-CH($R^2$)-NH2→$R^1$COCH($R^2$)NHCOCH($R^3$)$R^4$-COO-tbu→$R^1$COCH($R^2$)NHCOCH($R^3$)$R^4$-COOH $R^1$COCH($R^2$)NHCOCH($R^3$)$R^4$-COOH+OHsuccinNH2→$R^1$COCH($R^2$)NHCOCH($R^3$)$R^4$-COO-Nsuccin (A-B)

Fragment C+Fragment A-B
j) Treating a suspension of an optionally O-protected $R^5$ or its chloride in a solvent, e.g., DMF, sequentially with triethylamine and with a solution of the O-protected $R^1$-1-carbonyl-C2($R^2$)-carbamoyl-methylene($R^3$)-$R^4$-carboxylic acid 2,5-dioxo-pyrrolidin-1-yl ester in a solvent, e.g., DMF, to form an $R^1$-1-carbonyl-C2($R^2$)-carbamoyl-methylene($R^3$)-$R^4$-carbonyl-$R^5$ where $R^1$ and $R^5$ may be independently O-protected.

k) Hydrogenating $R^1$ and $R^5$, if $R^1$ and $R^5$ independently have an O-protecting group, with hydrogen gas and a catalyst, e.g., palladium hydroxide in activated carbon, to form (S,S,R)-(−)-actinonin or its derivative or analog.

$R^1$COCH($R^2$)NHCOCH($R^3$)$R^4$-COO-Nsuccin+$R^5$ (optionally O-protect)→$R^1$COCH($R^2$)NHCOCH($R^3$)$R^4$-CO-$R^5$(A-B-C)

Figure 2:
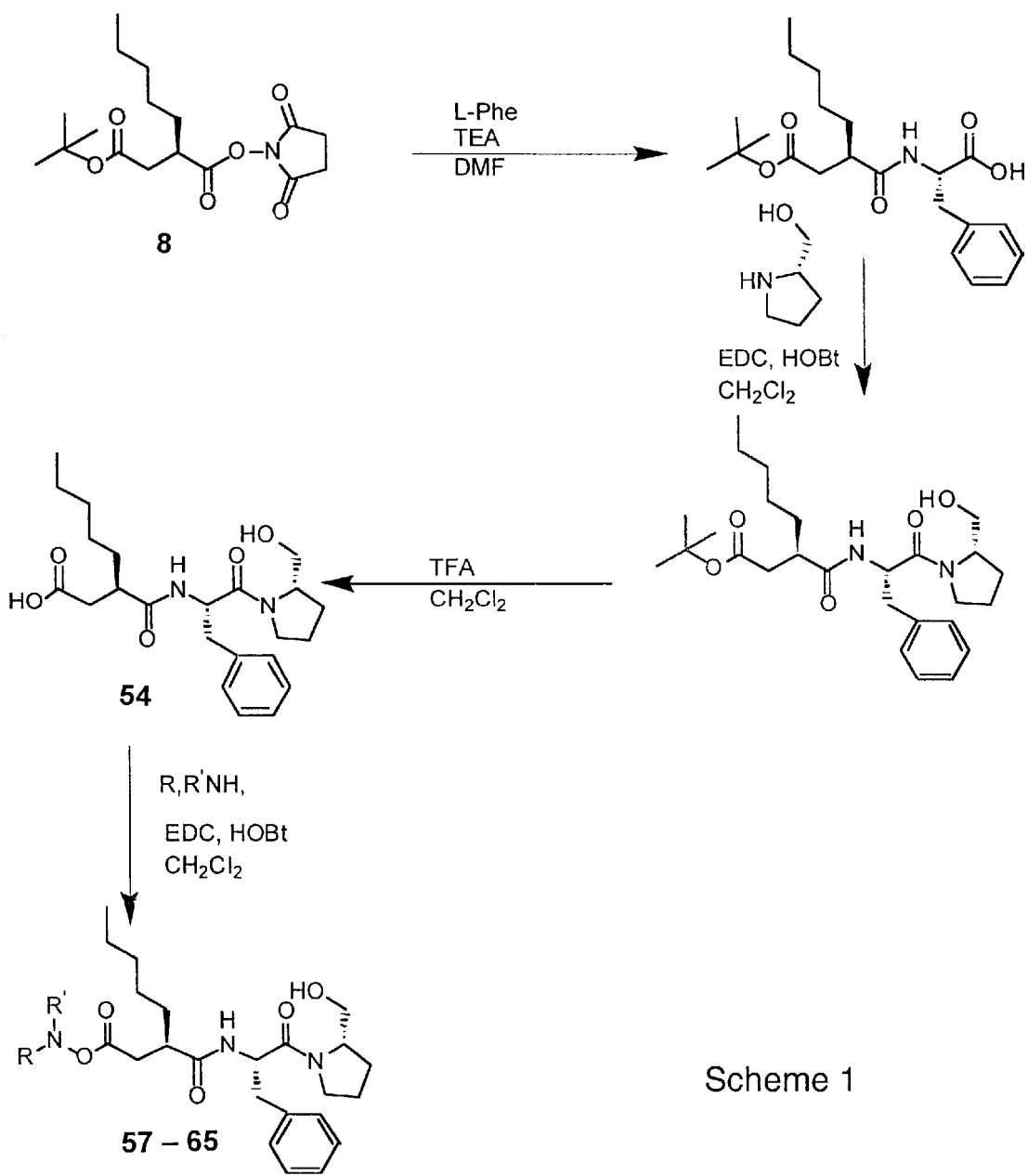
FIG. 2 depicts an alternative synthetic sequence for synthesizing and adding fragments A and C to fragment B for compounds having a benzyl functional group at $R^2$ (Scheme 1).

An alternative synthetic scheme can be used for those analogs or derivatives of actinonin where $R^2$ is benzyl and $R^5$ is a substituted amide, e.g., $NHOCH_3$, $N(CH_3)OCH_3$, $NHCH_2CH_3$, $NH(CH_2CH_3)_2$, $NHCH_2(2,4-(OCH3)_2Ph$, $NHCH_2(4-NO_2)Ph$, $NHN(CH_3)_2$, piperidine or 1-methyl-piperazine. In this instance L-phenylalanine is added to fragment B followed by 2-hydroxymethyl pyrrolidine. The t-butyl ester of Fragment B is removed and $R^1$ is added to form the compounds. Scheme 1 details the synthesis using structural formulas (FIG. 2).

Fragment B+L-phenylalanine
a) Treating a solution of L-phenylalanine in a solvent, e.g., DMF, sequentially with triethylamine and with the 2-pentylsuccinic acid 4-tert-butyl ester 4-(2,5-dioxo-pyrrolidin-1-yl) ester to form an 3-(1-Carboxy-2-phenyl-ethylcarbamoyl)-octanoic acid tert-butyl ester.

succinN-OCOCH(($CH2)_4CH_3$)-$CH_2$-COO-tbu+L-phe→HO-CO-CH($CH_2(C_6H_5)$)-NHCO-CH(($CH2)_4CH_3$)-$CH_2$-COO-tbu→

Adding $R^1$ or 2-hydroxymethyl pyrrolidine
b) Coupling 2-hydroxymethyl pyrrolidine to 3-(1-Carboxy-2-phenyl-ethylcarbamoyl)-octanoic acid tert-butyl ester in a solvent, e.g., methylene chloride, and in the presence of EDC and HOBT to form 3-[1-(2-hydroxymethyl-pyrrolidin-1-yl)-2benzylcarbamoyl]-octanoic acid 4-tert-butyl ester.
c) Treating a solution of 3-[1-(2-hydroxymethyl-pyrrolidin-1-yl)-2-benzylcarbamoyl]-octanoic acid 4-tert-butyl ester in a solvent, e.g., methylene chloride, with TFA to form 3-[1-(2-hydroxymethyl-pyrrolidin-1-yl)-2-benzylcarbamoyl]-octanoic acid. HOCOCH($CH_2(C_6H_5)$)-NHCO-CH(($CH2)_4CH_3$)-$CH_2$-COO-tbu+HOCH3-pyrrolidine+cleave tbu→

HOCH$_2$-Npyr-COCH($CH_2(C_6H_5)$)-NHCO-CH(($CH2)_4CH_3$)-$CH_2$-COOH

Adding $R^5$
d) Treating a suspension of $R^5$ in a solvent, e.g., methylene chloride, and in the presence of EDC and HOTS with a solution of 3-[1-(2-hydroxymethyl-pyrrolidin-1-yl)-2-benzyl carbamoyl]-octanoic acid in methylene chloride to form N4($R^5$)-N1-[1-benzyl-2(2-hydroxymethyl-pyrrolidin-1-yl)-2-oxo-ethyl]-2-pentyl-succinamide.

HOCH$_2$NpyrCOCH($CH_2(C_6H_5)$)-NHCO-CH(($CH2)_4CH_3$)-$CH_2$-COOH+$R^5$ →

HOCH$_2$NpyrCOCH($CH_2(C_6H_5)$)-NHCO-CH(($CH2)_4CH_3$)-$CH_2$-CO-$R^5$

It is also contemplated that these analogs are to be used as anti-tumor agents or for the use in the treatment of neoplastic diseases by the methods disclosed herein. It is specifically contemplated that pharmaceutical compositions may be prepared using the novel actinonin analogs of the present invention. In such a case, the pharmaceutical composition comprises the novel compounds of the present invention and a pharmaceutically acceptable carrier. When used in vivo for therapy, the compounds of the present invention are administered to the patient or an animal in therapeutically effective amounts, i.e., amounts that eliminate or reduce the tumor burden. A person having ordinary skill in this art would readily be able to determine, without undue experimentation, the appropriate dosages and routes of administration of the compounds and derivatives of the present invention.

The following examples are given for the purpose of illustrating various embodiments of the invention and are not meant to limit the present invention in any fashion.

EXAMPLE 1

General Methods and Materials

The $^1$H NMR and $^{13}$C NMR spectra were recorded on a Bruker 400 MHz using tetramethylsilane as the internal standard. High resolution mass spectra were obtained at the Mass Spectrometry Facility, University of California at Riverside. All reagents are obtained either from Sigma-Aldrich® or from Lancaster® and vacuum dried under $P_2O_5$ overnight before use. All solvents were reagent grade and distilled before use. Silica gel used for chromatography, MN-Kieselgel 60, was purchased from Brinkman Instruments Inc. All reactions were carried out under argon using glassware dried in an oven at 80° C. overnight and cooled under vacuum. The reaction mixtures were mechanically stirred using a magnetic stirring bar and stirring plate. Melting points were determined using a Mel-Temp II melting point apparatus fitted with a digital Barnart 115 thermocouple thermometer, and are uncorrected.

EXAMPLE 2

General Synthetic Protocol for Actinonin and Specific Analogs

For actinonin and those analogs or derivatives where $R^1$ is 2-methyl pyrrolidine, 2-hydroxymethyl pyrrolidine or 2-hydroxycarbamoyl pyrrolidine; and $R^2$ is methyl, $CH_2CH_3$, $(CH_2)_2CH_3$, $C(CH_3)_3$ and $R^3$ is $R^2$ or $C_{4-7}$alkyleneCH$_3$, the following protocol can be used:

a) Coupling of a suitably O-protected methoxypyrrolidine or a derivative thereof with a suitably N-protected amino acid 2,5-dioxo-pyrrolidinyl ester to form suitable N,O-protected methylpyrrolidine-1-carbonyl-2-methylamine.

b) Deprotection of the Nprotecting group with a suitable deprotecting agent such as trifluoracetic acid to yield the corresponding pyrrolidine-1-carbonyl-2-methylamine or a derivative thereof.

c) Treatment of a solution of a chiral auxiliary, such as 4-(S)-isopropyl-oxazolidin-2-one 2, with a solution of a suitable base, such as n-BuLi in hexanes, followed by the addition of an alkynoyl chloride to yield an alkynoyloxazolidinone.

d) Treatment of a solution of the alkynoyloxazolidinone with lithium diisopropylamide, or similar bases, followed by bromoacetic acid tert-butyl ester to yield an oxazolidine-carbonyl-alkynoic acid tert-butyl ester.

e) Treatment of a mixture of an oxazolidine-carbonyl-alkynoic acid tert-butyl ester in THF/water with hydrogen peroxide in water followed by lithium hydroxide in water to yield an alkylsuccinic acid 4-tert-butyl ester.

f) Treatment of a mixture of an alkylsuccinic acid 4-tert-butyl ester and hydroxysuccinimide 7 in a suitable solvent, such as dioxaneor dimethylformamide, with dicyclohexylcarbodiimide, or similar imides, to afford an alkylsuccinic acid 4-tert-butyl ester 4-(2,5-dioxo-pyrrolidin-1-yl) ester.

g) Treatment of a solution of a pyrrolidine-1-carbonyl-2-methylamine or a derivative thereof in a suitable solvent is treated with triethylamine followed by an alkyl-succinic acid 4-tert-butyl ester 4-(2,5-dioxo-pyrrolidin-1-yl) ester to yield a pyrrolidine-1-carbonyl-2-methylalkyl-carbamoyl-alkynoic acid tert-butyl ester or a derivative thereof.

h) Treatment of a pyrrolidine-1-carbonyl-2-methylalkyl-carbamoyl-alkynoic acid tert-butyl ester or a derivative thereof in a suitable solvent with trifluoroacetic acid to yield a pyrrolidine-1-carbonyl-2-methyl-alkylcarbamoyl-alkynoic acid or a derivative thereof.

i) Treatment of a pyrrolidine-1-carbonyl-2-methyl-alkylcarbamoyl-alkynoic acid or a derivative thereof and hydroxysuccinamide (7) with dicyclohexylcarbodiimide or any suitable imide to afford a pyrrolidine-1-carbonyl-2-methylalkylcarbamoyl)-alkynoic acid 2,5-dioxo-pyrrolidin-1-yl ester or a derivative thereof.

j) Treatment of a suspension of O-benzylhydroxyamine hydrochloride 18 in a suitable solvent with triethylamine followed by a solution of a pyrrolidine-1-carbonyl-2-methylalkylcarbamoyl)-alkynoic acid 2,5-dioxo-pyrrolidin-1-yl ester or a derivative thereof in a suitable solvent to afford N4-benzyloxy-N1-(1-(pyrrolidine-1-carbonyl)-2-methylalkyl-2-alkyl-succinamide or a derivative thereof.

k) Hydrogenation of a N-benzyloxy-N1-(1-(pyrrolidine-1-carbonyl)-2-methylalkyl-2-alkyl-succinamide or a derivative thereof with hydrogen gas and a suitable catalyst wherein actinonin or its analogs are thereby formed.

EXAMPLE 3

Specific synthesis of (S.R.R)-(−)-actinonin (S,R,R)-(−)-Actinonin is divided into three fragments A, B and C as previously disclosed. Fragment A, described as a pseudodipeptide, is composed of a (S)-prolinol and a (S)-valine. Fragment B, described as a succinnic acid derivative, is composed of a succinnic acid skeleton functionalized with an n-pentyl group at C2 or, alternatively, an (α-pentylsuccinate. Fragment C is a suitably protected hydroxylamine (FIG. 1B).

Synthesis of Fragment A

Fragment A is prepared by coupling a suitably N-protected and carboxy-activated (S)-valine and a suitably O-protected (S)-prolinol. The (α-pentylsuccinate fragment B is synthesized using an Evan's chiral auxiliary 2(13) (FIG. 1C).

Synthesis of Fragment B

Figure 3A:
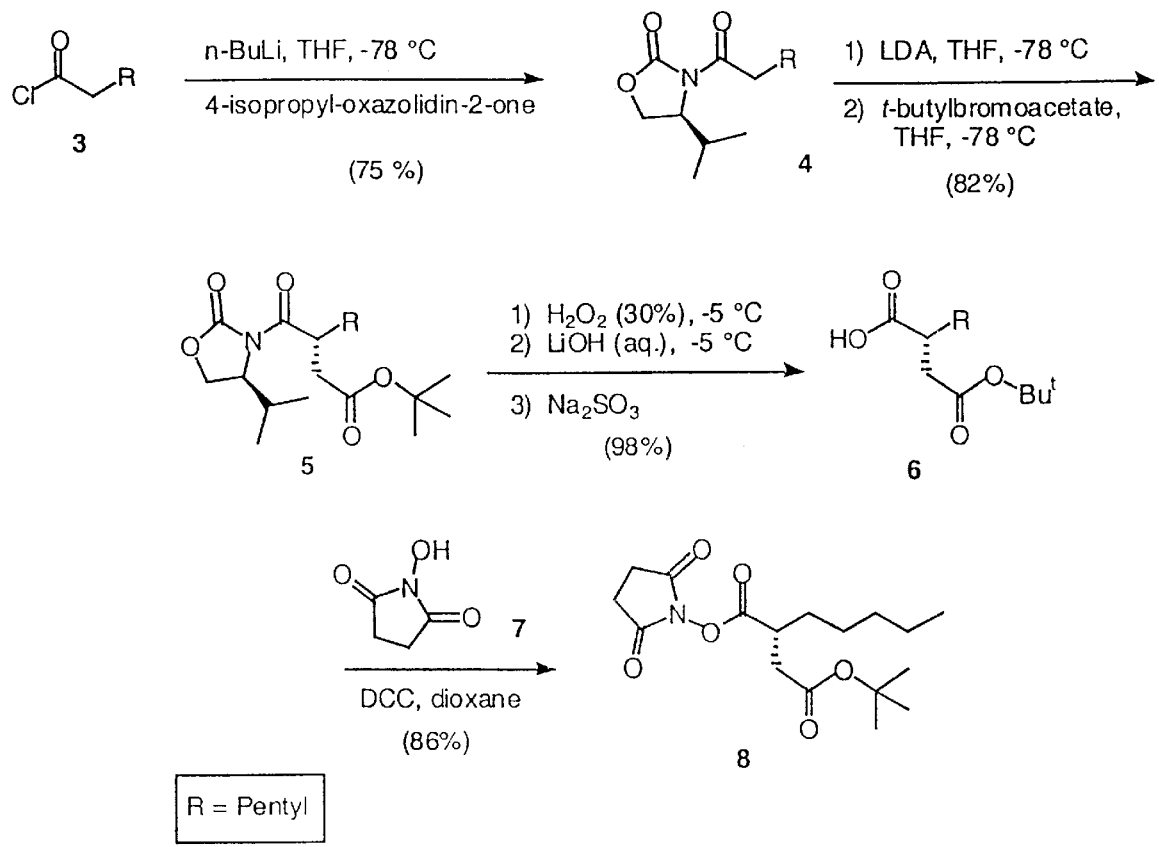
FIG. 3A depicts the synthetic sequences for the (α-pentylsuccinate fragment B (Scheme 2).

The synthesis of Fragment B is comprised of the following steps: (a) a solution of 4-(S)-isopropyl-oxazolidin-2-one 2 in THF at a temperature of −78° C. is treated with a solution of n-BuLi in hexanes, or any suitable base; (b) heptanoyl chloride 3 is added to the mixture to yield 3-heptanoyl-4-(S)-isopropyl-oxazolidin-2-one 4;(c) treatment of a solution of 4 in THF with lithium diisopropylamide, or similar bases, followed by bromoacetic acid tert-butyl ester yield 3-(4-(S)-isopropyl-2-oxo-oxazolidine-3-(S)-carbonyl)octanoic acid tert-butyl ester 5; (d) treatment of a mixture of 5 in THF/water with hydrogen peroxide in water followed by lithium hydroxide in water at 0° C. to yield 2-(R)-pentylsuccinic acid 4-tert-butyl ester 6; (e) treatment of a mixture of 6 and hydroxysuccinimide 7 in dimethylformamide or any suitable solvent, such as dioxane, with dicyclohexylcarbodiimide, or similar imides, to afford 2-(R)-pentylsuccinic acid 4-tert-butyl ester (should this be 1, if it is 4-t-butyl ester?)4-(2,5-dioxo-pyrrolidin-1-yl) ester 8(Scheme 2, FIG. 3A).

Synthesis of fragment A

Figure 3B:
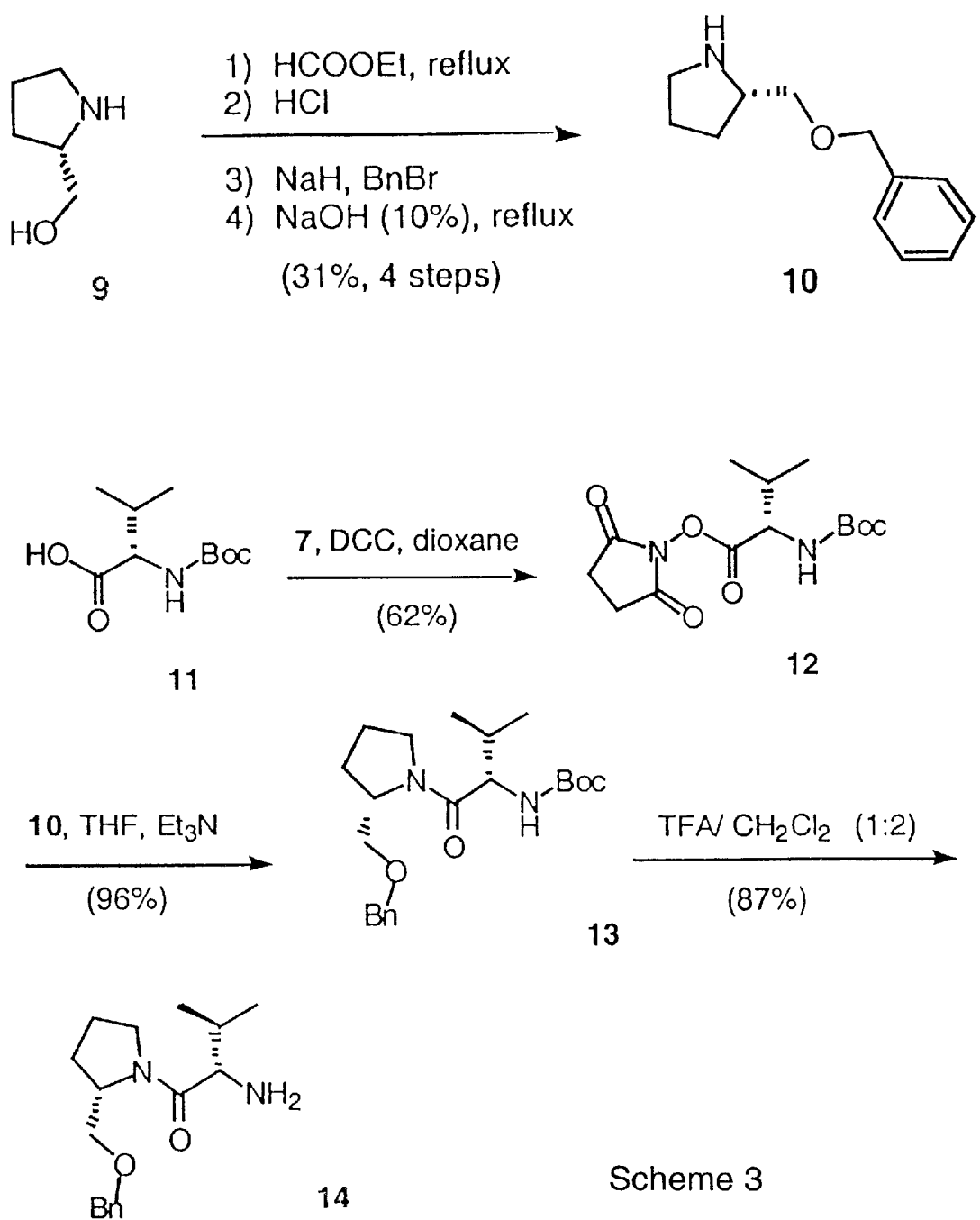
FIG. 3B depicts the synthetic sequences for the pseudo-dipeptide derivative of L-prolinol and L-valine fragment A (Scheme 3)

The synthesis is comprised of the following steps: (a) a solution of 2-(S)-benzyloxymethylpyrrolidine 10 in THF is treated with triethylamine followed by a solution of 2-tert-butoxycarbonylamino-3-methylbutyric acid 2,5-dioxo-pyrrolidin-1-yl 12 in THF to yield (1-(2-benzyloxymethyl-pyrrolidine-1-carbonyl)-2-methyl-propyl)-carbamic acid tert-butyl ester 13; which is then (b) dissolved in methylene chloride, or any suitable solvent, and treated with trifluoroacetic acid or any suitable Boc-deprotecting agent to yield 2-amino-1-(2-benzyloxymethylpyrrolidin-1-yl)-3-methylbutan-1-one 14 (Scheme 3, FIG. 3B).

A problem can occur with overhydrogenation involving the hydroxylamine group being converted to the corresponding amide. However, this could be avoided by carefully monitoring the amount of hydrogen consumed during hydrogenation. In some occassions, when the overreduction product is observed in TLC, the reaction is quenched, the product is isolated, and the starting material resubjected to hydrogenation.

Synthesis of (−)-actinonin using fragments A, B and C

Figure 3C:
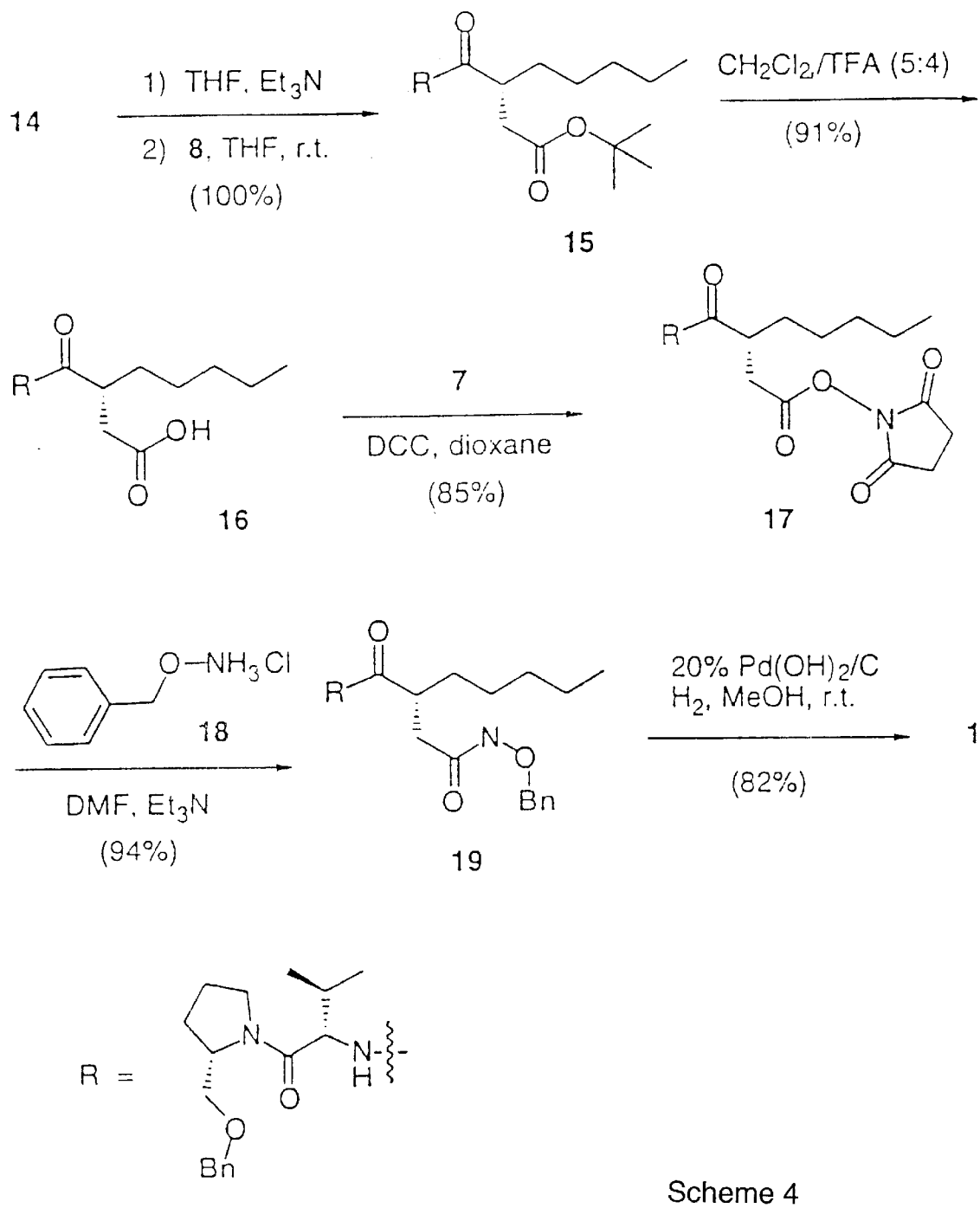
FIG. 3C depicts the synthetic sequences for the joining of fragments A, B and C to yield (S,S,R)-(-)-actinonin (Scheme 4).
Figure 4A:
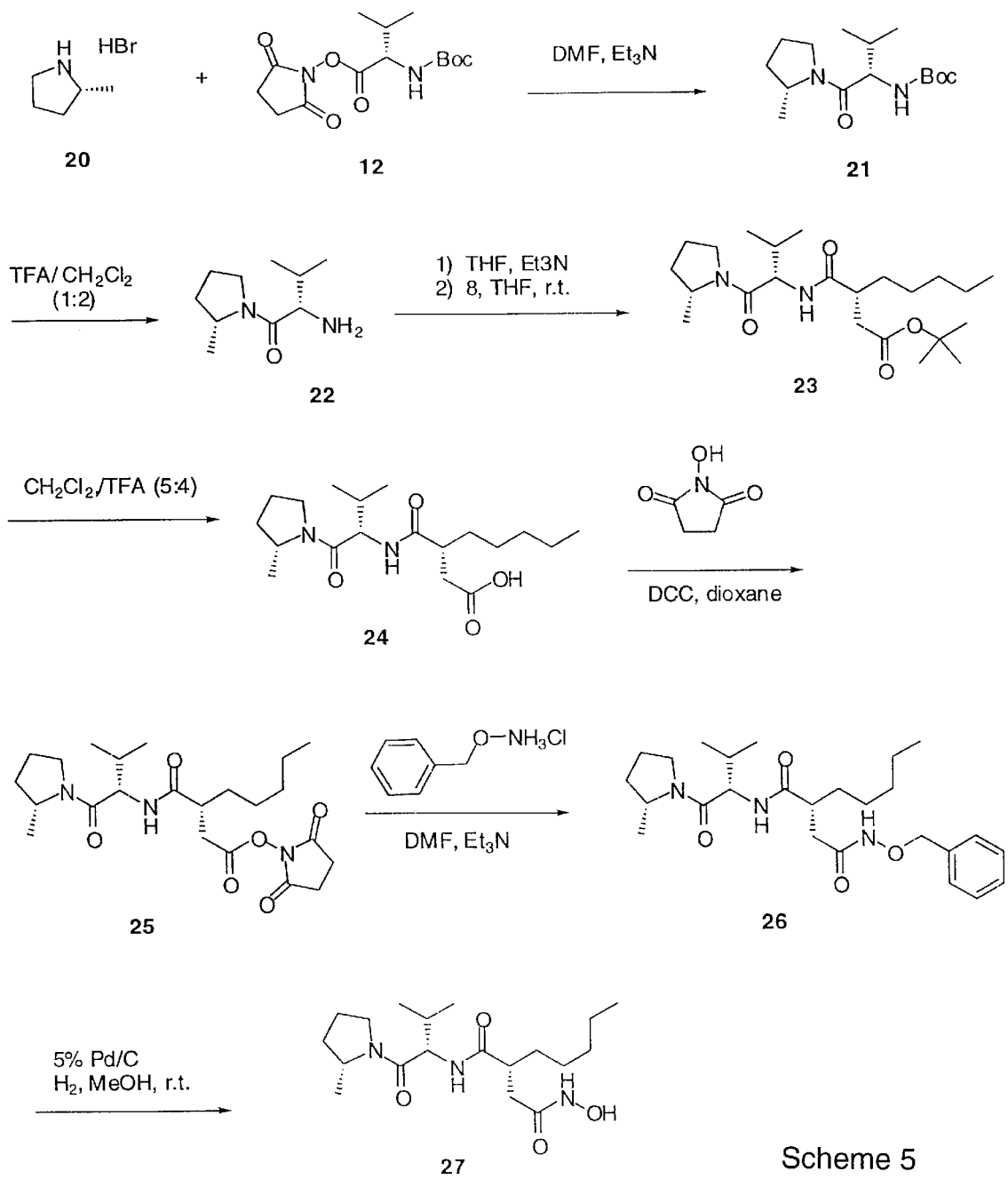
FIG. 4A shows the synthetic sequence of the actinonin analogs N4-hydroxy-N1-(1-(2-methyl-pyrrolidine-1-carbonyl)-3-methyl-propyl)-2-pentyl-succinamide (27) (Scheme 5).
Figure 4B:
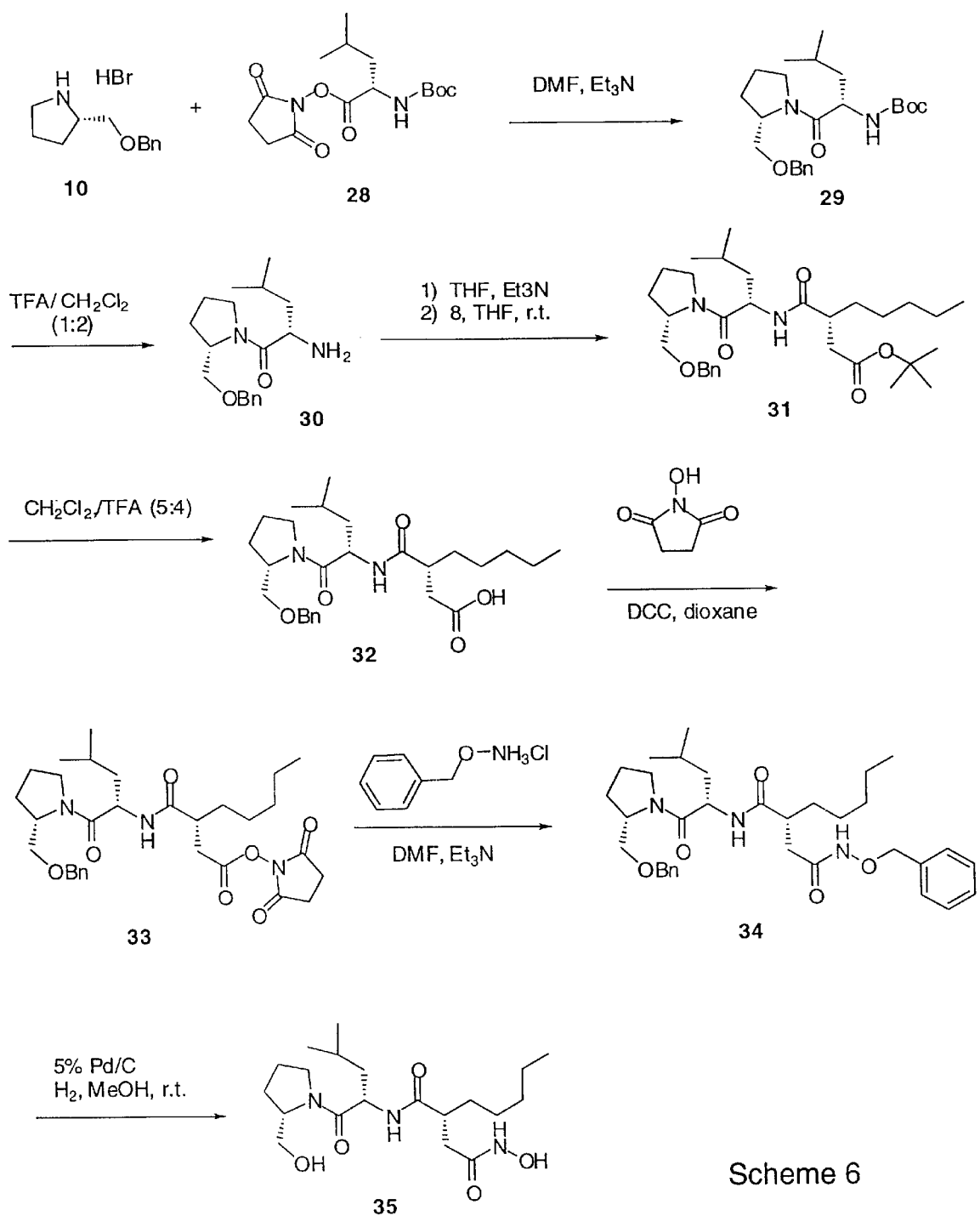
FIG. 4B shows the synthetic sequence of the actinonin analogs N4-hydroxy-N1-(1-(2-hydroxymethyl-pyrrolidine-1-carbonyl)-3-methyl-butyl)-2-pentyl-succinamide (35) (Scheme 6).

The coupling of fragment A and B is comprised of the following steps: (a) a solution of 14 in dimethylformide or any suitable solvent is treated with triethylamine followed by a solution of 8 in dimethylformamide or any suitable solvent to yield 3-(1-(2-(S)-benzyloxymethylpyrrolidine-1-carbonyl)-2-(S)-methylpropyl-carbamoyl)-octanoic acid tert-butyl ester 15; (b) treatment of 15 in dichloromethane with trifluoroacetic acid to yield 3-(1-(2-benzyloxymethyl-pyrrolidine-1-carbonyl)-2-methyl-propyl carbamoyl)-octanoic acid 16; (c) treatment of a solution 16 and hydroxysuccinamide 7 with dicyclohexylcarbodiimide or any suitable imide to afford 3-(1-(2-benzyloxymethyl-pyrrolidine-1-carbonyl)-2-methylpropylcarbamoyl)-octanoic acid 2,5-dioxo-pyrrolidin-1-yl ester 17; (d) fragment C is introduced by treatment of a suspension of O-benzylhydroxyamine hydrochloride 18 in dimethylformamide with triethylamine followed by a solution of 17 in dimethylformamide to afford N4-benzyloxy-N1-(1-(2-benzyloxymethyl-pyrrolidine-1-carbonyl)-2-methyl-propyl)-2-pentyl-succinamide 19. (f) hydrogenating 19 with hydrogen gas and palladium hydroxide in activated carbon wherein actinonin 1 is thereby formed (Scheme 4, FIG. 3C).

EXAMPLE 4

Synthesis of Specific Compounds in Schemes 1, 2 and 3 Synthesis of 3-heptanoyl-4-(S)-isopropyl-oxazolidin-2-one (4)

To a solution of oxazolidone (2) (30.2 g, 0.234 mol) in 400 mL THF at −78° C. was added n-BuLi (2.5 M in hexanes, 96.0 mL, 0.240 mol) dropwise over a period of 30 min. The solution was stirred at −78° C. for an hour. Heptanoyl chloride (37.15 g, 0.250 mol) was gradually added by syringe and the resulting solution stirred at −78° C. for 1 h and then warmed to 0° C. A saturated aqueous solution of $NH_4Cl$ (100 mL) was added and the mixture gradually warmed to room temperature. The mixture was extracted with ethyl acetate (3×20 mL) and the combined organic layers were washed with brine and dried over anhydrous $MgSO_4$. The solvent was removed by a rotary evaporation and the yellowish residue chromatographed on a silica gel column using Hexane/EtOAc (8:1) as the eluant to give 4 as a colorless oil (46.272 g, 0.192 mol, 82%). $^1H$ NMR (400 MHz, $CDCl_3$) δ0.87 (t, J=7.2 Hz, 3 H), 0.88 (d, J=16.9 Hz, 3 H), 0.90 (d, J=16.9 Hz, 3 H), 1.24–1.39 (m, 6 H), 1.59–1.69 (m, 2 H)2.31–2.43 (m, 1 H), 2.81–3.02 (m, 2 H), 4.19–4.29 (m, 2 H), 4.41–4.45 (m, 1 H); $^{13}C$ NMR (100 MHz, $CDCl_3$) δ13.9, 14.5, 17.9, 22.4, 24.3, 28.3, 28.7, 31.4, 35.4, 58.3, 63.2, 154.0, 173.4.

Synthesis of 3-(S)-(4-(S)-isopropyl-2-oxo-oxazolidine-3-carbonyl)-octanoic acid tert-butyl ester (5)

To a solution of 4(37.082 g, 0.154 mol) in THF (300 mL) at −78° C. is added LiHMDS in THF (1.0 M, 0.162 mol, 162 mL) via cannula. The solution is stirred at −78° C. for 1 h. tert-Butylbromoacetate is added and then stirred for 30 more minutes. It is then gradually warmed to 0° C. and stirred at this temperature for 30 min. To this solution is gradually added 100 mL saturated aqueous solution of $NH_4Cl$. The bulk of the THF is removed by rotary evaporation and the remaining mixture was extracted with $CH_2Cl_2$ (100 mL×3). The combined $CH_2Cl_2$ extracts is washed consecutively with 1N NaOH, 1 N HCl, saturated $NaHCO_3$, and brine. It is then dried over $MgSO_4$ and concentrated in vacuo. The residue is chromatographed in silica gel using hexane/ethyl acetate (5:1) as eluant to afford 5. $^1H$ NMR (400 MHz, $CDCl_3$) δ0.85 (t, J=6.8 Hz, 3 H), 0.91 (d, J=8.15 Hz, 3 H), 0.93 (d, J=8.15 Hz, 3 H), 1.18–1.35 (m, 6 H), 1.40 (s, 9 H), 1.35–1.49 (m, 1 H), 1.56–1.66 (m, 1 H), 2.31–2.39 (m, 1 H), 2.44 (dd, J=16.6, 4.5, 1 H), 2.73 (dd, J=16.6, 10.3, 1 H), 4.11–4.20 (m, 1 H), 4.44 (m, 1 H); $^{13}C$ NMR (75.45 MHz, $CDCl_3$) δ13.9, 14.4, 17.9, 22.4, 26.4, 27.9, 28.0, 31.4, 31.6, 31.7, 37.0, 39.2, 58.6, 62.9, 80.3, 153.5, 171.2, 175.8. HRMS calcd for $C_{19}H_{34}NO_5$ ($MH^+$): 356.2436. Found (DCI): 356.2418 (Δ=5.3 ppm).

Synthesis of 2-(R)-pentylsuccinic acid 4-tert-butyl ester (6)

A solution of 5 (25.5 g, 71.73 mmol) in THF (300 mL) and water (75 mL) under Ar is cooled to 0° C. To this is added via syringe $H_2O_2$ (30% in water, 30.6 mL, 0.300 mol) gradually over a period of 15 minutes. $LiOH \cdot H_2O$ (4.92 g, 0.12 mol) in water (150 mL) is added via syringe. The mixture is stirred for 3 h after which the septum is removed and $Na_2SO_3$ (37.8 g, 0.300 mol) in water (225 mL) is added slowly. The bulk of the THF is removed by rotavap at a bath temperature between 25–30° C. The residue is extracted with $CH_2Cl_2$ (100 ml×3). The combined organic layer is washed consecutively with 0.5 N HCl (100 mL), sat. $NaHCO_3$ (100 mL), water (100 mL) and brine ( 100 mL). The solution is then dried over $Na_2SO_4$ and concentrated in vacuo. The residue is recrystallized in hexane/ethyl acetate to afford the Evan's chiral auxiliary 2 as white needles. The aqueous layer from the first extraction was acidified to pH 1 and extracted with ethyl acetate (100 mL×3). The combined organic layer is washed with 0.5 N HCl (100 mL) and then brine (100 mL). It is then dried over $Na_2SO_4$ and concentrated to yield 6 as a colorless oil (17.198 g, 70.39 mmol, 98%). $^1H$ NMR (400 MHz, $CDCl_3$) δ0.88 (t, J=6.8 Hz, 3 H), 1.21–1.37 (m, 6 H), 1.43 (s, 9 H), 1.40–1.70 (m, 2 H), 2.61 (dd, J=9.3 Hz, 1 H), 2.38 (dd, J=16.4, 5.1, 1 H), 2.61 (dd, J=16.4, 9.3, 1 H), 2.78 (m, 1 H); $^{13}C$ NMR (100 MHz, $CDCl_3$) δ13.9, 17.5, 17.9, 22.3, 26.5, 27.9, 31.5, 37.0, 41.3, 94.9, 80.0, 171.1, 181.1. HRMS calcd for $C_{13}H_{25}O_4$ ($MH^+$): 245.1752. Found (DCI): 245.1766 (Δ=5.2 ppm).

Synthesis of 2-(R)-pentyl-succinic acid 4-tert-butyl ester 4-(2,5-dioxo-1pyrrolidin-1-yl) ester (8)

To a solution of 6 (7.149 g, 29.26 mmol) and N-hydroxysuccinimide (6.90 g, 60.0 mmol) in 1,4-dioxane (40 mL) at r.t. is added via cannula a solution of DCC ( 8.25 g, 40 mmol) in 1,4-dioxane (20 mL). The mixture is stirred overnight, afterwhich it is filtered through celite and the solids washed with acetone. The filtrate is concentrated in vacuo and the residue redissolved in acetone. The acetone solution is cooled to 0° C. and filtered again. The filtrate is concetrated in vacuo and dissolved in ethyl acetate/THF. The solution is washed with sat. solution of NaHCO$_3$ (100 mL) and then brine (100 mL). It is then dried over Na$_2$SO$_4$ and concentrated to yield 8 as a white solid (8.93 g, 25.16 mmol, 86%). $^1$H NMR (400 MHz, CDCl$_3$) δ0.85 (t, J=6.1 Hz, 3 H), 1.27–1.38 (m, 4 H), 1.43 (s, 9 H), 1.59–1.67 (m, 2 H), 1.71–1.78 (m, 2 H), 2.47 (dd, J=16.7, 8.0 Hz, 1 H), 2.72 (dd, J=16.7, 8.0, 1 H), 2.81 (bs, 4 H), 3.07–3.14 (m, 1 H); $^{13}$C NMR (100 MHz, CDCl$_3$) δ14.3, 19.4, 22.7, 25.9, 26.5, 28.3, 31.8, 32.1, 37.3, 39.5, 81.8, 169.3, 170.3, 170.8. HRMS calcd for C$_{17}$H$_{31}$N$_2$O$_6$ (MNH$_4^+$): 359.2181. Found (DCI): 359.2167 (Δ=4.2 ppm).

Synthesis of 2-(S)-benzyloxymethyl-pyrrolidine (10)

A solution of 2-S-methanol-pyrrolidine (10.0 g, 99.0 mmol) in ethylformate (50 mL) is refluxed for 3 h. It is then cooled and concentrated in vacuo to afford a yellowish oil which is taken in ethyl acetate (50 mL) and washed successively with 1N HCl (50 mL×3), sat. NaHCO$_3$ (50 mL), and brine (50 mL). The solution is dried over Na$_2$SO$_4$, concentrated in vacuo, and dried further overnight under vacuum. The yellowish oil is dissolved in THF (100 mL), cooled to 0° C., and treated with NaH (6.0 g, 0.250 mol). Benzyl bromide (34.2 g, 0.20 mol) is added dropwise. The mixture is stirred overnight after which it is cooled to 0° C. and a saturated solution of NH$_4$Cl is added slowly. The layers are separated and the THF layer is diluted with ethyl acetate (50 mL). This solution is washed with 1 N HCl (50 mL) and then brine (50 mL). The solution is then concentrated in vacuo. The residue is mixed with 10% NaOH (100 mL) and refluxed overnight. The mixture is then extracted with ethyl acetate (50 mL×3). The organic layers are combined and washed successively with 50 mL portions of 1 N HCl, sat. NaHCO$_3$, water, and brine. It is then dried over Na$_2$SO$_4$ and concentrated. The residue is chromatographed in silica gel using ethyl acetate as eluant to yield 10 as a yellowish oil (5.84 g, 30.6 mmol, 31%). $^1$H NMR (400 MHz, CDCl$_3$) δ1.33–1.38 (m, 1 H), 1.63–1.77 (m, 3 H), 2.75–2.81 (m, 1 H), 2.87–2.91 (m, 1 H), 3.22–3.46 (m, 3 H), 4.43–4.50 (m, 2 H) 7.20–7.28 (m, 5 H); $^{13}$C NMR (100 MHz, CDCl$_3$) δ24.7, 27.4, 33.6, 45.9, 57.4, 72.6, 73.3, 127.0, 127.1, 127.6, 127.8, 137.9.

Synthesis of (1-(2-benzyloxymethyl-pyrrolidine-1-carbonyl)-2-methyl-propyl)-carbamic acid tert-butyl ester (13)

To a solution of 10 (2.67 g, 14.0 mmol) and triethylamine (5 mL) in THF (10 mL) at r.t. is added a solution of 12 (4.40 g, 14.0 mmol) via cannula. After complete addition, the solution is stirred overnight. THF is removed in vacuo and the residue taken in ether. The ether solution is washed successively with 50 mL portions of 0.5 N HCl, sat. NaHCO$_3$, water, and brine. It is then dried over Na$_2$SO$_4$ and concentrated. The residue is chromatographed in silica gel using hexane/ethyl acetate (3:1:) as eluant to yield 13 as a colorless oil (4.75 g, 12.16 mmol, 87%). %). $^1$H NMR (400 MHz, CDCl$_3$) δ0.88 (t, J=6.7 Hz, 3 H), 0.94 (d, J=6.7, 3 H), 1.43 (s, 9 H), 1.84–2.09 (m, 5 H), 2.00–2.10 (m, 1 H); 2.28–2.36 (m 1 H), 2.49 (dd, J=16.7, 6.2 Hz, 1 H), 2.74 (dd, J=16.7, 8.2, 1 H), 3.47–3.52 (m, 1 H), 3.55–3.60 (m, 2 H), 3.62–3.68 (m, 2 H), 4.25–4.29 (m, 1 H), 4.32–4.35 (m, 1 H), 4.48–4.52 (m, 2 H), 5.26–5.31 (m, 1 H), 7.25–7.36 (m, 5 H); $^{13}$C NMR (100 MHz, CDCl$_3$) δ17.8, 19.8, 24.8, 27.6, 28.7, 31.9, 48.0, 57.0, 57.3, 70.4, 73.5, 79.7, 127.3, 127.5, 128.2, 138.9, 157.1, 172.5. HRMS calcd for C$_{22}$H$_{34}$N$_2$O$_4$ (MH$^+$): 391.2596. Found (DCI): 391.2612 (Δ=–3.9 ppm).

Synthesis of 2-amino-1-(2-benzyloxymethyl-pyrrolidin-1-yl)-3-methyl-butan-1-one (14)

To a solution of 13 (4.75 g, 12.16 mmol) in CH$_2$Cl$_2$ (10 mL) is added TFA (10 mL). The solution is stirred for 1 h and then quenched with a saturated solution of NaHCO$_3$ (50 mL). The mixture is extracted with CH$_2$Cl$_2$ (50 mL×2). The combined organic layers are washed with 50 mL portions of sat. NaHCO$_3$, water, and brine. It is then dried over Na$_2$SO$_4$ and concentrated to give pure 14 as a yellow oil (3.07 g, 10.56 mmol, 87%). $^1$H NMR (400 MHz, CDCl$_3$) δ0.87 (t, J=6.8 Hz, 3 H), 0.91 (d, J=6.8, 3 H), 1.65–1.79 (m, 2 H), 1.79–1.96 (m, 2 H), 1.99–2.17 (m, 1 H); 3.27–3.45 (m 1 H), 3.46–3.54 (m, 1 H), 3.59–3.62 (m, 1 H), 4.33–4.38 (m, 1 H), 4.46–4.54 (m, 2 H), 7.27–7.42 (m, 5 H); $^{13}$C NMR (100 MHz, CDCl$_3$) δ16.9, 19.8, 24.4, 27.2, 47.2, 56.6, 58.3, 70.1, 73.1, 127.3, 127.4, 128.2, 138.4, 173.8. HRMS calcd for C$_{17}$H$_{27}$N$_2$O$_2$ (MH$^+$): 291.2072. Found (DCI): 291.2088 (Δ=–5.3 ppm).

Synthesis of 3-(R)-(1-(2-(S)-benzyloxymethyl-pyrrolidine-1-carbonyl)-2-(S)-methyl-propylcarbamoyl)-octanoic acid tert-butyl ester (15)

To solution of 14 (3.06 g, 10.56 mmol), triethylamine (5 mL), and THF (100 mL) is added a solution of 8 in THF (40 mL). The solution is stirred overnight and then washed with 50 mL portions of 1 N HCl, sat. NaHCO$_3$, water, and brine. It is then dried over Na$_2$SO$_4$ and concentrated in vacuo. The residue is chromatographed in silica gel using hexane/ethyl acetate (3:1) as eluant to give 15 as a clear colorless oil (5.25 g, 10.17 mmol, 96%). $^1$H NMR (400 MHz, CDCl$_3$) δ0.85 (t, J=6.3 Hz, 3 H), 0.92 (d, J=13.1, 3 H), 0.94 (d, J=13.1, 3 H), 1.09–1.34 (m, 6 H), 1.43 (s, 9 H), 1.58–1.66 (m, 2 H), 1.68–1.76 (m, 2 H), 1.85–1.97 (m, 4 H), 2.00–2.10 (m, 1 H); 2.28–2.36 (m 1 H), 2.49 (dd, J=16.7, 6.2 Hz, 1 H), 2.74 (dd, J=16.7, 8.2, 1 H), 3.10–3.21 (m, 2 H), 3.46–3.52 (m, 2 H), 3.67–3.77 (m, 2 H), 4.28–4.33 (m, 2 H), 4.49 (s, 2 H), 4.59–4.63 (m, 2 H), 7.29–7.37 (m, 5 H); $^{13}$C NMR (100 MHz, CDCl$_3$) δ13.8, 17.4, 19.0, 22.3, 24.3, 25.3, 27.2, 27.9, 31.5, 32.2, 34.8, 37.8, 42.9, 47.5, 55.3, 56.5, 69.9, 73.0, 80.3, 127.3, 127.4, 128.2, 170.3, 171.5, 174.4. HRMS calcd for C$_{30}$H$_{49}$N$_2$O$_5$ (MH$^+$): 517.3641. Found (DCI): 517.3613 (Δ=5.5 ppm).

Synthesis of 3-(R )-(1-(2-(S)-benzyloxymethyl-pyrrolidine -1-carbonyl)-2-(S)-methyl-propylcarbamoyl)-octanoic acid (16)

To a solution of 15 (5.16 g, 10.0 mmol) in CH$_2$Cl$_2$ (10 mL) is added TFA (10 mL). The solution is stirred for 2 h and then diluted with CH$_2$Cl$_2$ (50 mL). The solution is washed with 50 mL portions of 1 N HCl, water, and brine. It is then dried over Na$_2$SO$_4$ and concentrated to give pure 16 as a clear colorless oil (4.19 g, 9.10 mmol, 91%). $^1$H NMR (400 MHz, CDCl$_3$) δ0.84 (t, J=6.8 Hz, 3 H), 0.91 (d, J=13.1, 3 H), 0.93 (d, J=13.1, 3 H), 1.14–1.29 (m, 6 H), 1.30–1.37 (m, 2 H), 1.39–1.46 (m, 2 H), 1.91–2.15 (m, 4 H), 3.08–3.18 (m, 1 H), 3.56–3.59 (m, 2 H), 3.45 (dd, J=16.8, 6.1 Hz, 1 H), 3.78 (dd, J=16.8, 8.1, 1 H), 3.89–3.92 (m, 1 H); 4.26–4.37 9 (m, 1 H), 4.48 (s, 2 H), 4.57 (t, J=8.7 Hz, 1 H), 7.28–7.40 (m, 5 H); $^{13}$C NMR (100 MHz, CDCl$_3$) δ13.7, 18.2, 18.7, 22.3, 24.2, 26.3, 26.6, 30.9, 31.3, 32.2, 34.1, 36.1, 40.9, 42.2, 48.8, 57.0, 58.1, 69.5, 73.7, 127.4, 127.6, 128.3, 137.2, 171.5, 176.1, 176.8. HRMS calcd for C$_{26}$H$_{40}$N$_2$O$_5$ (MH$^+$): 461.3015. Found (DCI): 461.3023 (Δ=–1.6 ppm).

Synthesis of 3-(R)-(1-(2-(S)-benzyloxymethyl-pyrrolidine-1-carbonyl)-2-(S)-methyl-propylcarbamoyl)-octanoic acid 2.5-dioxo-pyrrolidin-1-yl ester (17)

To a solution of 16 (4.19 g, 9.10 mmol) and N-hydroxysuccinimide (1.88 g, 16.38 mmol) in 1,4-dioxane (30 mL) is added a solution of DCC ( 2.472 g, 12 mmol) in 12 mL dioxane. The mixture is stirred overnight and filtered thru celite. The solids are washed with cold acetone and the filtrate concentrated in vacuo. The residue is redissolved in acetone, cooled to 0° C., and filtered. The filtrate is concentrated and the residue taken in ether. The solution is washed with 50 mL portions of 0.5 N HCl, sat. NaHCO$_3$, water, and brine. It is then dried over Na$_2$SO$_4$ and concentrated. The residue is chromatographed in silica gel using hexane/ethyl acetate (1:10) as eluant to yield 17 as a white solid (4.313 g, 7.73 mmol, 85%). $^1$H NMR (400 MHz, CDCl$_3$) δ0.84 (t, J=6.7 Hz, 3 H), 0.91 (d, J=13.1, 3 H), 0.93 (d, J=13.1, 3 H), 1.05–1.16 (m, 2 H), 1.21–1.30 (m, 2 H), 1.57–1.62 (m, 2 H), 1.64–1.72 (m, 2 H), 1.87–2.10 (m, 4 H), 2.43–2.51 (m 1 H), 2.67–2.79 (m, 2 H), 3.45–3.50 (m, 2 H), 3.55 (dd, J=9.2, 2.8, 1 Hz, 1 H), 3.63 (dd, J=9.2, 5.6 Hz, 1 H), 4.30 (bs, 4 H), 4.48 (s, 2 H); 4.60 (t, J=8.5 Hz, 2 H), 7.27–7.35 (m, 5 H); $^{13}$C NMR (100 MHz, CDCl$_3$) δ13.8, 17.7, 19.2, 22.3, 25.5, 26.5, 26.8, 31.2, 32.4, 33.5, 36.7, 42.7, 47.8, 55.7, 56.8, 69.7, 73.1, 127.3, 127.5, 128.3, 138.2, 167.4, 170.7, 173.2, 175.0, 175.3. HRMS calcd for C$_{30}$H$_{44}$N$_3$O$_7$ (MH$^+$): 558.3179. Found (FAB): 558.3184 (Δ=0.5 ppm).

Synthesis of N4-benzyloxy-N1-(1-(2-(S)-benzyloxymethyl-pyrrolidine-1-carbonyl)-2-(S)-methyl-propyl)-2-(R)-pentylsuccinamide (19)

A solution of 17 (2.50 g, 4.49 mmol) in DMF (20 mL) is added, via cannula, to a suspension of 18 (1.12 g, 7.0 mmol) in triethylamine (10 mL) and DMF (20 mL). The mixture is stirred overnight afterwhich it is diluted with CH$_2$Cl$_2$ (50 mL) and washed with water (50 mL×2), 1 N HCl (50 mL), sat. NaHCO$_3$ (50 mL), water (50 mL), and brine (50 mL). The solution is dried over Na$_2$SO$_4$ and concentrated in vacuo. The residue is chromatographed in silica gel using hexane/ethyl acetate (1:10) as eluant to give 19 as a white solid (2.50 g, 4.42 mmol, 98% yield). $^1$H NMR (400 MHz, CDCl$_3$) δ0.83 (t, J=6.7 Hz, 3 H), 0.90 (d, J=13.1, 3 H), 0.93 (d, J=13.1, 3 H), 1.05–1.16 (m, 2 H), 1.21–1.30 (m, 2 H), 1.57–1.62 (m, 2 H), 1.64–1.72 (m, 2 H), 1.87–2.10 (m, 4 H), 2.43–2.51 (m 1 H), 2.67–2.79 (m, 2 H), 3.45–3.50 (m, 2 H), 3.55 (dd, J=9.2, 2.8, 1 Hz, 1 H), 3.63 (dd, J=9.2, 5.6 Hz, 1 H), 4.48 (s, 2 H); 4.60 (t, J=8.5 Hz, 2 H),4.87 (s, 2 H), 7.27–7.37 (m, 10 H); $^{13}$C NMR (100 MHz, CDCl$_3$) δ13.7, 18.2, 18.7, 22.3, 24.2, 26.3, 26.6, 30.9, 31.3, 32.2, 34.1, 36.1, 40.9, 42.2, 48.8, 57.0, 58.1, 69.5, 69.5, 73.7, 127.3, 127.5, 127.6, 128.3, 128.4, 128.5, 128.8 138.2, 171.9, 176.3, 177.2. HRMS calcd for C$_{33}$H$_{48}$N$_3$O$_5$ (MH$^+$): 566.3593. Found (FAB): 566.3573 (Δ=−2.1 ppm).

Synthesis of (S,S,R)-actinonin (1)

Pd(OH)$_2$/C (Pearlman's catalyst) (525 g, ~100 mg Pd content) in a 100 mL two-neck round bottom flask fitted with a stirring bar is activated by repeated evacuation of the flask and introduction of hydrogen gas. Once activated, a solution of 19 (2.50 g, 4.42 mmol) in methanol (50 mL) is added via syringe. The amount of hydrogen consumed is measured and the reaction is monitored closely by TLC. Once the amount of calculated hydrogen gas is exceeded and the starting material totally consumed, the hydrogen is removed and the reaction mixture filtered through celite. The solids are washed with liberal amounts of methanol. The methanol is removed in vacuo and the residue chromatographed in silica gel using CH$_2$Cl$_2$/CH$_3$OH (10:1) as eluant to afford 1 as an off-white solid (3.757 g, 9.74 mmol, 82%). (α)$^{21}$$_D$−51 (c=0.19, CH$_3$OH); m.p. 141.5–142.0° C., mixed m.p. 141.7–142.4° C., (m.p. of commercial sample (Sigma®) 140.6–141.4° C.) (lit.[2] 148–149° C.). $^1$H NMR (400 MHz, CDCl$_3$) δ0.71 (t, J=6.6 Hz, 3 H), 0.95–1.18 (m, 11 H), 1.25–1.46 (m, 2 H), 1.50–1.61 (m, 1 H), 1.51–1.72 (m, 1 H), 1.76–1.95 (m, 2 H), 1.96–2.06 (m, 1 H), 2.22–2.34 (m, 1 H), 2.68 (dd, J=13.8, 5.6 Hz, 1 H), 3.04 (dd, J=13.8, 7.5 Hz, 1 H), 3.51–3.62 (m, 2 H), 3.82–3.91 (m, 1 H), 4.08–4.18 (m, 2 H), 4.52–4.60 (m, 1 H), 4.95 (t, J=8.4 Hz, 1 H); $^{13}$C NMR (100 MHz, CDCl$_3$) δ16.3, 21.1, 21.9, 24.1, 24.9, 26.7, 29.5, 29.9, 33.6, 34.1, 35.5, 39.5, 45.6, 50.3, 59.3, 62.4, 65.5, 171.3, 174.4, 177.8. m/z 386.3 (MH$^+$).

EXAMPLE 5

Synthesis of Analogs of (S.S.R)-actinoninN4-hydroxy-N1-(1-(2-methyl-pyrrolidine-1-carbonyl)-3-methyl-propyl)-2-pentyl-succinamide (27)

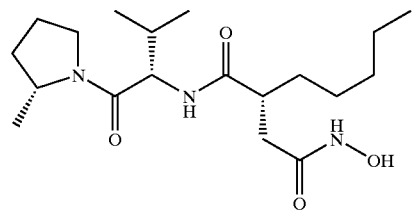

The synthesis is comprised of the following steps: (a) a solution of 2-(S)-methylpyrrolidine hydrobromide 20 in dimethylformamide is treated with triethylamine followed by a solution of 2-tert-butoxycarbonylamino-3-methylbutyric acid 2,5-dioxo-pyrrolidin-1-yl 12 in dimethylformamide to yield (1-(2-methylpyrrolidine-1-carbonyl)-2-methyl-propyl)-carbamic acid tert-butyl ester 21; which is then (b) dissolved in methylene chloride, or any suitable solvent, and treated with trifluoroacetic acid to yield 2-amino-1-(2-methylpyrrolidin-1-yl)-3-methylbutan-1-one 22; (c) a solution of 22 in dimethylformamide is treated with triethylamine followed by a solution of 8 in dimethylformamide to yield 3-(1-(2-(S)-methylpyrrolidine-1-carbonyl)-2-(S)-methylpropyl-carbamoyl)-octanoic acid tert-butyl ester 23; (d) treatment of 23 in dichloromethane with trifluoroacetic acid to yield 3-(1-(2-methyl-pyrrolidine-1-carbonyl)-2-methyl-propylcarbamoyl)-octanoic acid 24; (e) treatment of a solution 24 and hydroxysuccinamide 7 with dicyclohexylcarbodiimide to afford 3-(1-(2-methyl-pyrrolidine-1-carbonyl)-2-methylpropylcarbamoyl)-octanoic acid 2,5-dioxo-pyrrolidin-1-yl ester 25; (f) treatment of a suspension of O-benzylhydroxyamine hydrochloride 18 in dimethylformamide with triethylamine followed by a solution of 25 in dimethylformamide to afford N4-benzyloxy-N1-(1-(2-benzyloxymethyl-pyrrolidine-1-carbonyl)-2-methyl-propyl)-2-pentyl-succinamide 26. (g) hydrogenating 26 with hydrogen gas and palladium in activated carbon wherein N4-hydroxy-N1-(1-(2-methyl-pyrrolidine-1-carbonyl)-3-methyl-propyl)-2-pentyl-succinamide 27 is thereby formed.

N4-hydroxy-N1-(1-(2-hydroxymethyl-pyrrolidine-1-carbonyl)-3-methyl-butyl)-2-pentyl-succinamide (35)

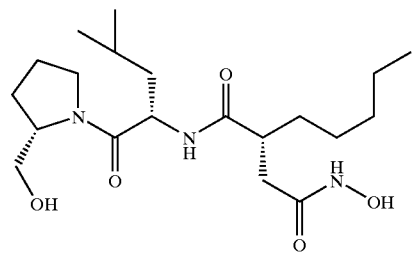

The synthesis, is comprised of the following steps: (a) a solution of 2-(S)-benzyloxymethylpyrrolidine 10 in THF is treated with triethylamine followed by a solution of 2-tert-butoxy carbonyl amino-4-methylpentanoic acid 2,5-dioxopyrrolidin-1-yl 28 in THF to yield (1-(2-benzyloxymethyl-pyrrolidine-1-carbonyl)-3-methyl-isobutyl)-carbamic acid tert-butyl ester 29; which is then (b) dissolved in methylene chloride and treated with trifluoroacetic acid to yield 2-amino -1-(2-benzyloxymethylpyrrolidin-1-yl)-4-methylpentan-1-one 30; (c) a solution of 30 in dimethylformide or any suitable solvent is treated with triethylamine followed by a solution of 8 in dimethylformamide or any suitable solvent to yield 3-( 1-(2-(S)-benzyloxymethylpyrrolidine-1-carbonyl)-2-(S)-methyl isopropyl-carbamoyl)-octanoic acid tert-butyl ester 31; (d) treatment of 31 in dichloromethane with trifluoroacetic acid to yield 3-(1-(2-benzyloxymethyl-pyrrolidine-1-carbonyl)-2-methyl-isobutyl carbamoyl)-octanoic acid 32; (e) treatment of a solution 32 and hydroxysuccinamide with dicyclohexylcarbodiimide or any suitable imide to afford 3-(1-(2-benzyloxymethyl-pyrrolidine-1-carbonyl)-2-methylisocarbamoyl)-octanoic acid 2,5-dioxo-pyrrolidin-1-yl ester 33; (f) treatment of a suspension of O-benzylhydroxyamine hydrochloride 18 in dimethylformamide with triethylamine followed by a solution of 33 in dimethylformamide to afford N4-benzyloxy-N1-(1-(2-benzyloxymethyl-pyrrolidine-1-carbonyl)-2-methyl-isobutyl)-2-pentyl-succinamide 34. (g) hydrogenating 34 with hydrogen gas and palladium hydroxide in activated carbon wherein N4-hydroxy-N1-(1-(2-hydroxymethyl-pyrrolidine-1-carbonyl)-3-methyl-butyl)-2-pentyl-succinamide 35 is thereby formed.

EXAMPLE 6

Structure and nomenclature of additional analogs of (S.S.R)-actinonin

N4-hydroxy-N1-(1-(2-hydroxymethyl-pyrrolidine-1-carbonyl)-3-methyl-butyl)-2-pentyl succinamide (41)

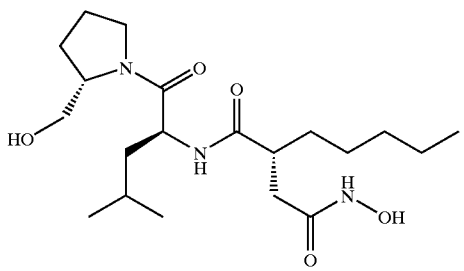

N1-(1-benzyl-2-(2-hydroxymethyl-pyrrolidin-1-yl)-2-oxo-ethyl)-N4-hydroxy-2-pentyl-succinamide (42)

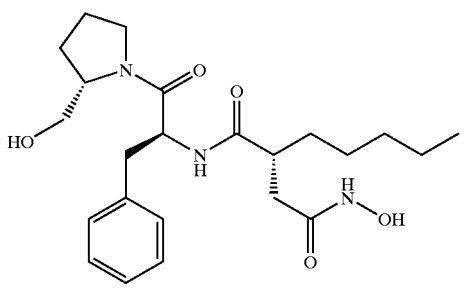

N4-hydroxy-N1-(1-(4-hydroxy-benzyl)-2-(2-hydroxymethyl-pyrrolidin-1-yl)-2-oxo-ethyl)-2-pentyl-succinamide (43)

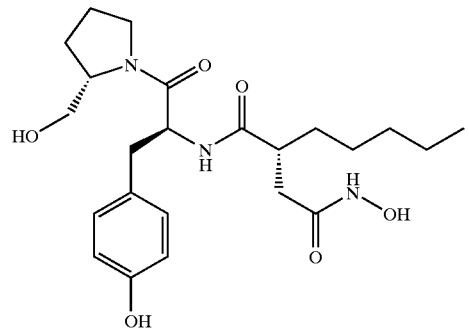

N4-hydroxy-N1-(2-(2-hydroxymethyl-pyrrolidin-1-yl)-1(1H-indol-3-yl-methyl)-2-oxo-ethyl)-2-pentyl-succinamide (44)

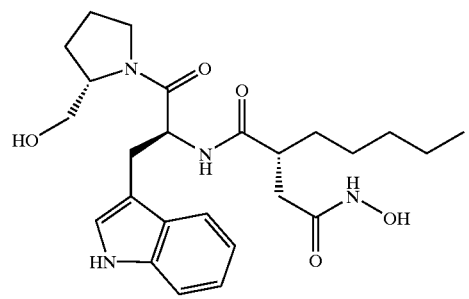

N1-(5-amino-1-(2-hydroxymethyl-pyrrolidine-1-carbonyl)-pentyl)-N4-hydroxy-2-pentyl-succinamide (45)

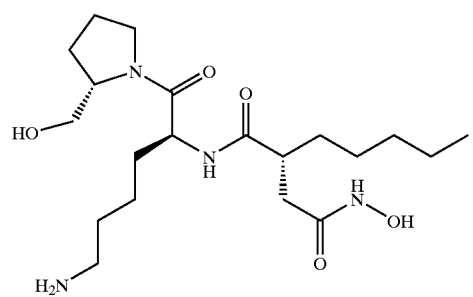

21

N4-hydroxy-N1-(1-(2-hydroxymethyl-piperidine-1-carbonyl)-2-methyl-propyl)-2-pentyl-succinamide (46)

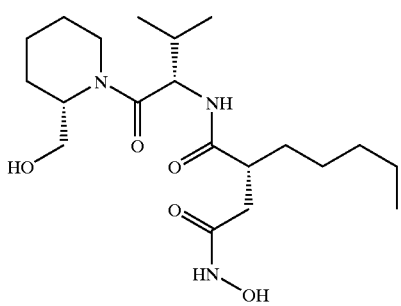

N4-hydroxy-N1-(1-(2-hydroxycarbamoyl-pyrrolidine-1-carbonyl)-3-methyl-butyl)-2-pentyl succinamide (47)

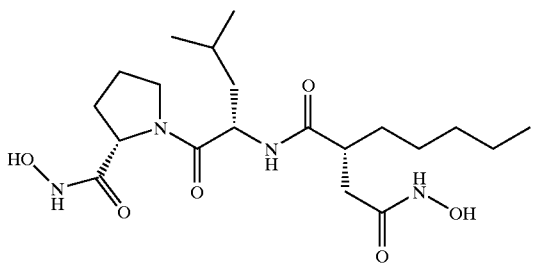

N4-hydroxy-N1-(1-(2-hydroxymethyl-pyrrolidine-1-carbonyl)-2-methyl-propyl)-2-methyl-succinamide (48)

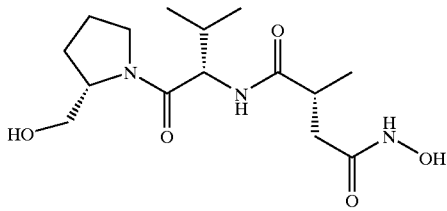

N1-(1-(2-hydroxymethyl-pyrrolidine-1-carbonyl)-3-methyl-butyl)-2-pentyl-succinamide (49)

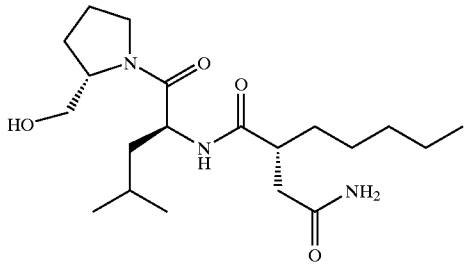

22

N1-(1-benzyl-2-(2-hydroxymethyl-pyrrolidin-1-yl)-2-oxo-ethyl)-2-pentyl-succinamide (50).

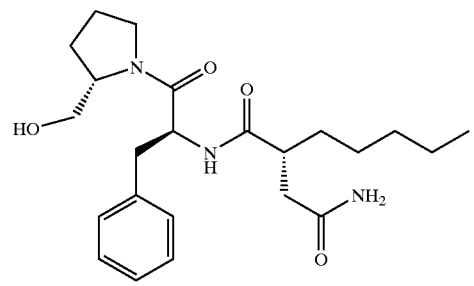

N1-(1-(2-methyl-pyrrolidine-1-carbonyl)-2-methyl-propyl)-2-pentyl-succinamide (51)

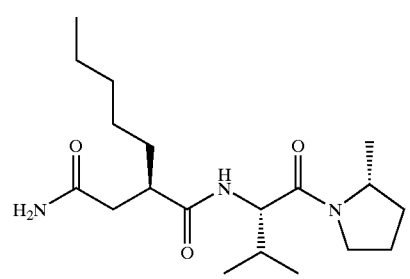

N4-hydroxy-N1-(1-benzyl-2-(,2-methyl-pyrrolidin-1-yl)-2-oxo-ethyl-2-pentyl-succinamide (52)

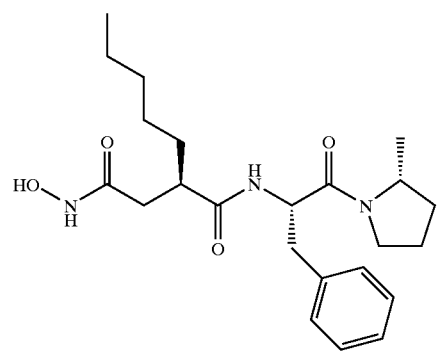

N4-hydroxy-N1-(1-(2-methylamine-pyrrolidine-1-carbonyl)-2-methyl-propyl)-2-pentyl-succinamide (53)

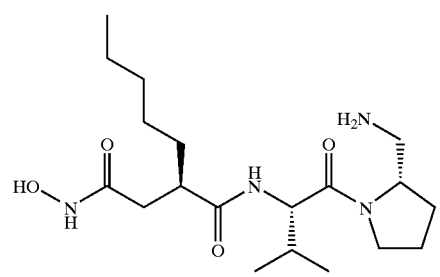

23

3-[1-(2-hydroxymethyl-pyrrolidin-1-yl)-2-benzylcarbamoyl]-octanoic acid (54)

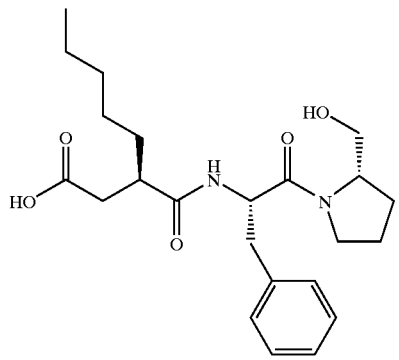

N4-hydroxy-N1-(1-(methyl-2-carboxy-pyrrolidine-1-carbonyl)-2-methyl-propyl)-2-pentyl-succinamide (55)

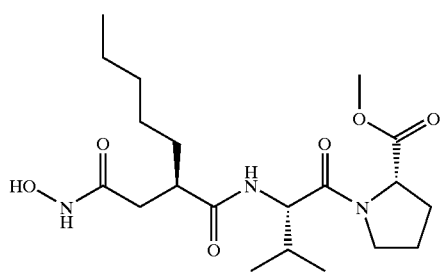

N4-hydroxy-N1-(1-(2-carboxy-pyrrolidine-1-carbonyl)-2-methyl-propyl)-2-pentyl-succinamide (56)

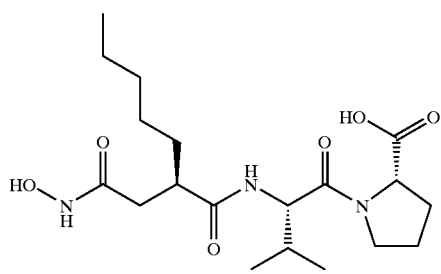

24

N4,N4-diethyl-N1-(1-benzyl-2-(2-hydroxymethyl-pyrrolidin-1-yl)-2-oxo-ethyl-2-pentyl-succinamide (57)

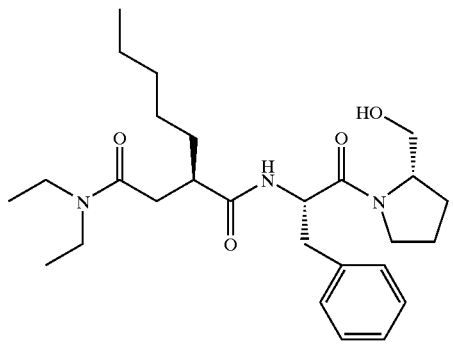

N4-ethyl-N1-(1-benzyl-2(2-hydroxymethyl-pyrrolidin-1-yl)-2-oxo-ethyl-2-pentyl-succinamide (58)

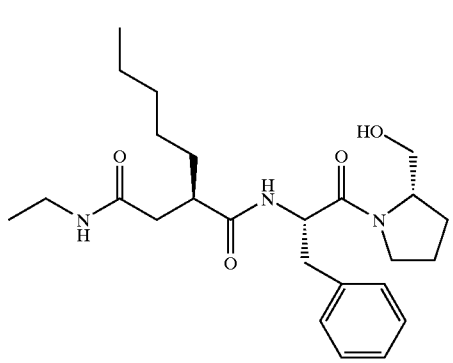

N4-(2,4-methoxybenzyl)-N1-(1-benzyl-2-(2-hydroxymethyl-pyrrolidin-1-yl)-2-oxo-ethyl-2-pentyl-succinamide (59)

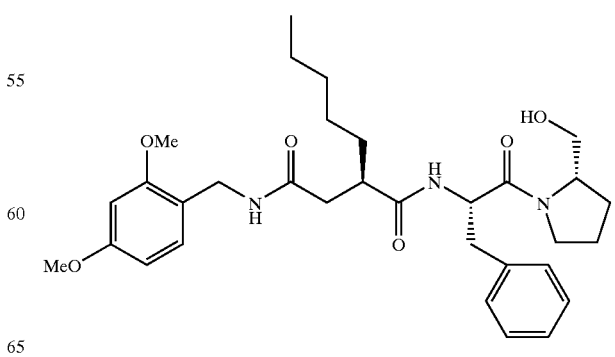

25

2-(N',N'-dimethyl-hydrazinocarbonylmethyl)-
heptanoic acid [1-benzyl-2-(2-hydroxymethyl-
pyrrolidin-1-yl)-2-oxo-ethyl]-amide (60)

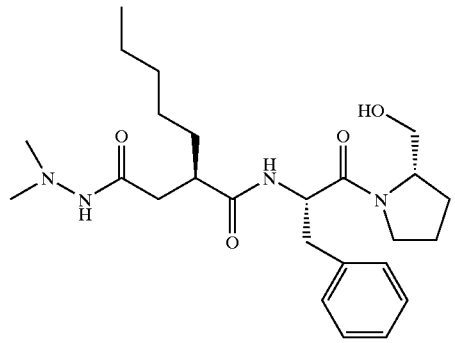

N4-(4-nitrobenzyl)-N1-(1-benzyl-2-(2-
hydroxymethyl-pyrrolidin-1 1-yl)-2-oxo-ethyl-2-
pentyl-succinamide (61)

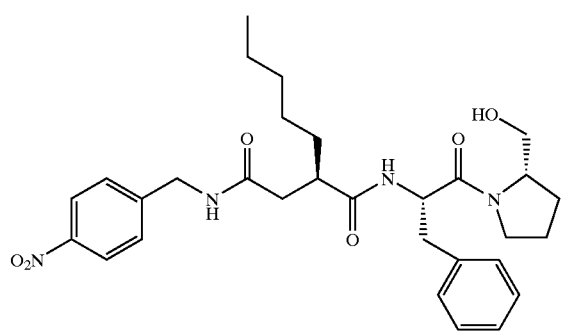

2-[2-(4-methyl-piperazin-1-yl)-2-oxo-ethyl]-
heptanoic acid [1-benzyl -2-(2-hydroxymethyl-
pyrrolidin-1-yl)-2-oxo-ethyl]-amide (62)

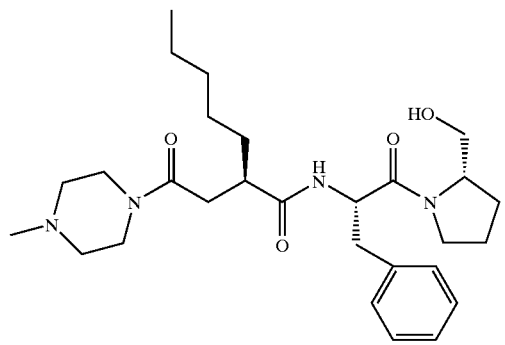

26

N4-(methoxy)-N1-(1-benzyl-2-(2-hydroxymethyl-
pyrrolidin-1-yl) -2-oxo-ethyl-2-pentyl-succinamide
(63)

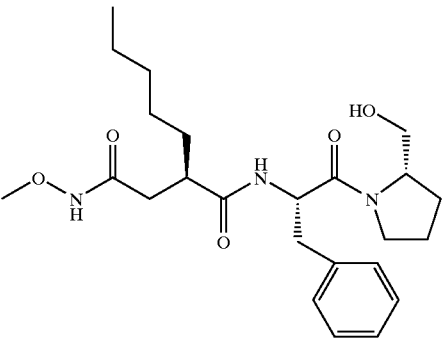

N4-(piperidin-1-carbonyl)-N1-(1benzyl-2(2-
hydroxymethyl-pyrrolidin -1-yl)-2-oxo-ethyl-2-
pentyl-succinamide (64)

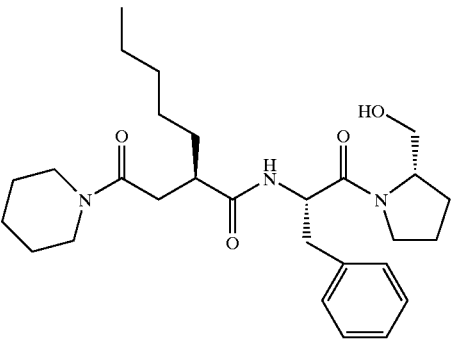

N4,N4-methoxymethyl-N1-(1-benzyl-2-(2-
hydroxymethyl-pyrrolidin -1-yl)-2-oxo-ethyl-2-
pentyl-succinamide (65)

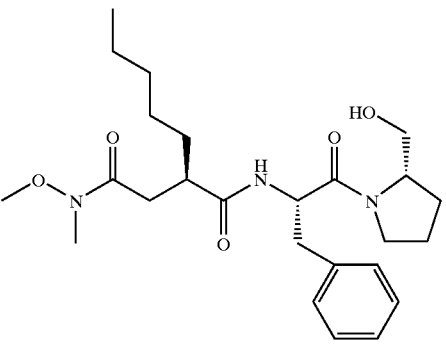

EXAMPLE 7

Cytotoxicity and Anti-tumor Activity of Actinonin

The therapeutic use of the compounds of the present invention in treatment of neoplastic diseases is illustrated. Actinonin was assayed for cytotoxity in human ovarian carcinoma, prostate carcinoma, mammary carcinoma, head and neck squamous cell carcinoma (HNSSC), non-small-cell-lung-cancer adenocarcinoma (NSCLC-AdCa), and non-small-cell-lung-cancer squamous cells (NSCLC-SSC) (15). Actinonin was also tested against acute mylegenous leukemia (AML) cells. The results are shown in Table 2. Actinonin is remarkably cytotoxic in the $\mu$M range against all the cell lines tested. These growth inhibitory properties provide for the use of these compounds as anti-tumor agents or for the use in the treatment of neoplastic diseases.

TABLE 2

Summary of cell culture data with actinonin[a]

| Cell line | Histology | IC$_{50}$ ($\mu$M ± SEM) | n Value |
|---|---|---|---|
| A2780 | Ovarian Ca | 4.8 ± 1 | 3 |
| TSU-PR[1] | Prostate Ca | 9.1 ± 1.5 | 3 |
| PC-3 | Prostate Ca | 10.0 ± 1 | 3 |
| DU-145 | Prostate Ca | 17.03 | 3 |
| HL-60 | PML (CML?) | 6.8 ± 1 | 4 |
| MDA-MB468 | Mammary Ca | 7.1 ± 1 | 4 |
| SK-BRIII | Mammary Ca | 7.9 ± 1 | 3 |
| HT1080 | HNSSC | 11.0 ± 2 | 4 |
| SK-LC-8 | NSCLC-AdCa | 14.0 ± 2 | 3 |
| SK-LC-16 | NSCLC-SSC | 12.0 ± 2 | 3 |

[a]Cells were grown for 5 days ± varying concentrations of actinonin.
Cell number were determined by XTT assay on an automatic plate reader.

Actinonin was also evaluated against the CWR22 human prostate tumor xenografted in nude mice (15). The results are summarized in Table 3. Actinonin shows excellent tumor growth inhibition at a dose slightly below the maximum tolerated dose (MTD) for the mouse.

TABLE 3

Anti-tumor activity of actinonin against the CWR22 human prostate tumor in nude mice.[a]

| R$_x$ (mg/kg) | Change in weight (%) | Ave. Tumor Diameter (mm ± SEM) | Change in tumor Vol. (mm$^3$) | Inhibition T/C % |
|---|---|---|---|---|
| — | | 13.3 ± 2 | +1190 | |
| 300 ip | −2 | 5.4 ± 1 | +36 | 97 |
| 600 ip | −3 | 7.1 ± 2 | +142 | 88 |

Initial tumor diameter = 4.4 + 0.3 min (45 mm$^3$)

EXAMPLE 8

Evaluation of Actinonin and Its Analogs Against Daudi Lymphomic and HL-60 Leukemic Cells Actinonin was purchased from Sigma (St. Louis, Mo.). Biotinylated-Actinonin and all analogs were synthesized. Actinonin stock solution was 5 mg/ml in 10% ethanol. Biotinylated-actinonin and all other analogs were diluted in 10% DMSO to give stock solutions in the range of 1–20 mg/ml.

Cell Lines and Culture Conditions

Daudi (B lineage Burkitt's lymphoma, CD13 negative) and HL60 (acute myeloid leukemia, CD13 positive) cells were maintained in culture using RPMI 1640 supplemented with 10% heat-inactivated FBS (Omega Scientific, Inc., Tarzana, Calif.) and 1% L-glutamine (Gibco/Invitrogen, Carlsbad, Calif.) at 37° C. in a humidified atmosphere of 5% $CO_2$. Cell viability was higher than 90%, and cells were free of mycoplasma contamination.

Inhibition of Tritiated Thymidine Incorporation

An aliquot of 200 ul of cells (10,000 cells/well) was washed and incubated at 37° C. in 96-well plates in the presence or absence of actinonin/analogs. Serial dilutions were made in complete media. After 5 days of incubation, 50 ul of 10 uCi/mL tritiated thymidine (PerkinElmer, Boston, Mass.) was added to each well and allowed to incorporate for 5 hours. Plates were frozen at −80° C. overnight and cells were harvested onto filtermats (Wallac, Finland) using a semi-automatic harvester (Skatron, Sterling, Va.). Filtermats were counted in a 1205 Betaplate™ liquid scintillation counter (Wallac, Finland). Tables 4 and 5 show the results of the actinonin analogs on cell viability. The reference numbers refer to those analogs disclosed in Example 6. Compounds 35, 42, 48, 52, 53, and 56 are effective at inhibiting cell growth.

TABLE 4

| | 5 day thymidine incorporation | |
|---|---|---|
| Compound | Daudi IC50 (ug/mL) | HL60 IC50 (ug/mL) |
| Actinonin | 2.6 | 4.1 |
| Biotin-Actinonin | >100 | >100 |
| #35 | 5.7 | 7.1 |
| #49 | >50 | >50 |
| #51 | 6.6 | 6.9 |
| #42 | 5.8 | 7.1 |
| #48 | 8.0 | 10.5 |
| #52 | 1.2 | 5.2 |
| #53 | 7.0 | 10.0 |
| Biotin-Act | 20.0 | 50.0 |
| #54 | ND | >100 |
| #57 | ND | >100 |
| #58 | ND | >100 |
| #59 | ND | >100 |
| #60 | ND | 90.0 |
| #61 | ND | >100 |
| #62 | ND | >100 |
| #63 | ND | >100 |
| #64 | ND | >100 |
| #65 | ND | >100 |
| Calpeptin | 6.0 | 50.0 |
| DL-Thiorphan | >100 | >100 |
| #55 | 0.4016 | 2.773 |
| #56 | >100 | >100 |

TABLE 5

| | 5 day thymidine incorporation | |
|---|---|---|
| Compound | Daudi IC50 (uM) | HL60 IC50 (uM) |
| Actinonin | 6.7 | 10.6 |
| Biotin-Actinonin | >138 | >138 |
| #35 | 14.1 | 17.7 |
| #49 | >130 | >130 |
| #51 | 18.7 | 19.5 |
| #42 | 12.9 | 15.8 |
| #48 | 22.4 | 29.5 |

TABLE 5-continued

|  | 5 day thymidine incorporation | |
| --- | --- | --- |
| Compound | Daudi IC50 (uM) | HL60 IC50 (uM) |
| #52 | 2.7 | 12.1 |
| #53 | 18.2 | 26.0 |
| Biotin-Act | 27.6 | 69.1 |
| #54 | ND | >239 |
| #57 | ND | >211 |
| #58 | ND | >225 |
| #59 | ND | >176 |
| #60 | ND | 195.5 |
| #61 | ND | >181 |
| #62 | ND | >200 |
| #63 | ND | >224 |
| #64 | ND | >206 |
| #65 | ND | >217 |
| Calpeptin | 16.6 | 137.9 |
| DL-Thiorphan | >395 | >395 |
| #55 | 0.97 | 6.7 |
| #56 | >251 | >251 |

Corrected concentrations for cuvette dilution (1/50) in PDF assay

The following references are cited herein:
1. Gordon, et al., *Nature*, Vol. 195, pg. 701 (1962).
2. Tieku, et al., *Biological Pharmacology* 1992, 44, 1725.
3. Fujii, et al., *Biol. Pharm. Bull.,* 1996, 19, 6.
4. Xu, Y., Lai, L. T., Gabrilove, J. L., Scheinberg, D. A. *Clinical Cancer Research,* 1998, 4, 171.
5. Sayama, et al., *Cancer Letters,* 1995, 171.
6. Bouboutou, R., Lelievre, Y., Boiziau, J., Cartwright, T. in *Second Forum on Peptides*, Eds. A. Aubry, M. Marraud, B. Vitoux. Collogue INSERM: John Libbey Eurotext Ltd., 1989, 174, 341.
7. Harper, E. *Ann. Rev. Biochem,* 1980, 49, 1063.
8. Gordon, et al., *J. Chem. Soc. Perkin Trans* 1. 1975, 819–824.
9. Umezawa, et al., *J. Antibiotics,* 1985, 38, 1629–1630.
10. Faucher, et al., *J. Antibiotics,* 1987, 40, 1757–1761.
11. Anderson, et al., *J. Chem. Soc. Perkin Trans* 1. 1975, 825–830.
12. Bashiardes, G., Bodwell, G. J., Davies, S. G. *J. Chem. Soc. Perkin Trans.* 1, 1993, 459–469.
13. Evans, et al., *J. Am. Chem. Soc.* 1982, 104, 1737.
14. Gage, J. R., Evans, D. A. *Org, Synth.* 1989, 68, 83.
15. Sirotnak, F. M., DeGraw, J. I., Colwell, W. T., Piper, J. R. *Cancer Chemother. Pharmacol* 1998, 42, 313.
16. Broek, L. A. G. M. van den, Porskamp, P. A. T. W., Haltiwanger, R. C., Zwanenburg, B. *J. Org. Chem.,* 1984, 49, 1691–1695.
17. Giglione, C., Serero, A., Pierre, M., Boisson, B., and Meinnel, T. *The EMBO Journal* 2000, 19(21):5916–29.
18. Dirk, L. M. A., Williams, M. A., and Houtz, R. L. *Plant Physiology,* 2001, 127:97–107.
19. Bracchi-Ricard, V., Nguyen, K. T., Zhou, Y., Ravi Rajagopalan, P. T., Chakrabarti, D., and Pei, D. *Archives of Biochemistry and Biophysics,* 2001, 396(2):162–170.

Any patents or publications mentioned in this specification are indicative of the levels of those skilled in the art to which the invention pertains. Further, these patents and publications are incorporated by reference herein to the same extent as if each individual publication was indicated to be incorporated specifically and individually by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A chemical compound comprising an analog or a derivative of (S,S,R)-(−)-actinonin having the structure:

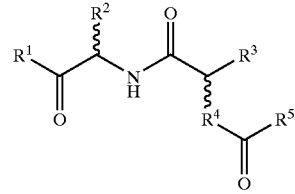

wherein $R^1$ is an optionally substituted or halogenated pyrrolidine, piperidine or piperazine;

$R^2$ is methyl, $CH_2CH_3$, $(CH_2)_2CH_3$, $C(CH_3)_3$, phenyl, 3,4-dichlorophenyl, biphenyl, benzyl, 4-hydroxybenzyl, piperidine, N-Boc-4-piperidine, $CH_2$-(N-Boc-4-piperidine), 4-tetrahydropyran, $CH_2$-4-tetrahydropyran, 3-methyl indolyl, 2-naphthyl, 3-pyridyl, 4-pyridyl, 3-thienyl;

$R^3$ is $R^2$ or $C_{3-8}$alkyl, $R^4$ is $C_{1-3}$alkyl; and $R^5$ is $NH_2$, OH, NHOH, $NHOCH_3$, $N(CH_3)OH$, $N(CH_3)OCH_3$, $NHCH_2CH_3$, $NH(CH_2CH_3)$, $NHCH_2(2,4-(OCH3)_2Ph$, $NHCH_2(4-NO_2)Ph$, $NHN(CH_3)_2$, proline, or 2-hydroxymethyl pyrrolidine.

2. The chemical compound of claim 1 wherein:

$R^1$ is pyrrolidine optionally substituted with 2-methylamino, 2-hydroxycarbamoyl, one of 2- or 3-hydroxymethyl, one of 2- or 3-methyl, ethyl, benzyl or phenyl, one of 2,3-, 2,4-, or 2,5-dimethyl, 2,5-diethyl, one of methyl-, ethyl-, t-butyl- or benzyl-3-carboxylate, or methyl-(2-methyl-5-carboxylate);

piperidine optionally substituted with 2- or 3-methyl or ethyl, one of methyl-, ethyl-, or benzyl- 2-, 3-, 4-carboxylate; or piperazine optionally substituted with 1-benzyl, N-t-boc, 1-furfuryl, 1-isonicotinoyl, or -one of pyridin-2-, 3- or 4-ylmethyl;

or pharmaceutically acceptable salts or hydrates thereof.

3. The chemical compound of claim 2, wherein said compound is N4-hydroxy-N1-(1-(2-methyl-pyrrolidine-1-carbonyl)-3-methyl-propyl)-2-pentyl-succinamide, N4-hydroxy-N1-(1-(2-hydroxymethyl-pyrrolidine-1-carbonyl)-3-methyl-butyl)-2-pentyl-succinamide, N4-hydroxy-N1-(1-(2-hydroxymethyl-pyrrolidine-1-carbonyl)-3-methyl-butyl)-2-pentyl succinamide, N1-(1-benzyl-2-(2-hydroxymethyl-pyrrolidin-1-yl)-2-oxo-ethyl)-N4-hydroxy-2-pentyl-succinamide, N4-hydroxy-N1-(1-(4-hydroxy-benzyl)-2-(2-hydroxy methyl-pyrrolidin-1-yl)-2-oxo-ethyl)-2-pentyl-succinamide, N4-hydroxy-N1-(2-(2-hydroxymethyl-pyrrolidin-1-yl)-1(1H-indol-3-yl-methyl)-2-oxo-ethyl)-2-pentyl-succinamide, N1-(5-amino-1-(2-hydroxymethyl-pyrrolidine-1-carbonyl)-pentyl)-N4-hydroxy-2-pentyl-succinamide, N4-hydroxy-N1-(1-(2-hydroxymethyl-piperidine-1-carbonyl)-2-methyl-propyl)-2-pentyl-succinamide, N4-hydroxy-N1-(1-(2-hydroxycarbamoyl-pyrrolidine-1-carbonyl)-3-methyl-butyl)-2-pentyl succinamide, N4-hydroxy-N1-(1-(2- hydroxymethyl-pyrrolidine-1-carbonyl)-2-methyl-propyl)-2-methyl-succinamide, N1-(1-(2-hydroxymethyl-pyrrolidine-1-carbonyl)-3-methyl-butyl)-2-pentyl-succinamide, N1-(1-benzyl-2-(2-hydroxymethyl-pyrrolidin-1-yl)-2-oxo-ethyl)-2-pentyl-succinamide, N1-(1-(2-methyl-pyrrolidine-1-carbonyl)-2-methyl-propyl)-2-pentyl-succinamide, N4-hydroxy-N1-(1-benzyl-2-(2-methyl-pyrrolidin-1-yl)-2-oxo-ethyl-2-pentyl-succinamide, N4-hydroxy-N1-(1-(2-methylamine-pyrrolidine-1-carbonyl)-2-methyl-propyl)-2-pentyl-succinamide, 3-[1-(2-hydroxymethyl-pyrrolidin-1-yl)-2-benzylcarbamoyl]-octanoic acid (54), N4-hydroxy-N1-(1-(methyl-2-carboxy-pyrrolidine-1-carbonyl)-2-methyl-propyl)-2-pentyl-succinamide, N4-hydroxy-N1-(1-(2-carboxy-pyrrolidine-1-carbonyl)-2-methyl-propyl)-2-pentyl-succinamide, N4,N4-diethyl-N1-(1-benzyl-2-(2-hydroxymethyl-pyrrolidin-1-yl)-2-oxo-ethyl-2-pentyl-succinamide, N4-ethyl-N1-(1-benzyl-2-(2-hydroxymethyl-pyrrolidin-1-yl)-2-oxo-ethyl-2-pentyl-succinamide, N4-(2,4-methoxybenzyl)-N1-(1-benzyl-2-(2-hydroxymethyl-pyrrolidin-1-yl)-2-oxo-ethyl-2-pentyl-succinamide, 2-(N',N'-dimethyl-hydrazinocarbonylmethyl)-heptanoic acid [1-benzyl-2-(2-hydroxymethyl-pyrrolidin-1-yl)-2-oxo-ethyl]-amide, N4-(4-nitrobenzyl)-N1-(1-benzyl-2-(2-hydroxymethyl-pyrrolidin-1-yl)-2-oxo-ethyl-2-pentyl-succinamide, 2-[2-(4-methyl-piperazin-1-yl)-2-oxo-ethyl]-heptanoic acid [1-benzyl-2-(2-hydroxymethyl-pyrrolidin-1-yl)-2-oxo-ethyl]-amide, N4-(methoxy)-N1-(1-benzyl-2-(2-hydroxy methyl-pyrrolidin-1-yl)-2-oxo-ethyl-2-pentyl-succinamide, N4-(piperidin-1-carbonyl)-N1-(1-benzyl-2-(2-hydroxymethyl-pyrrolidin-1-yl)-2-oxo-ethyl-2-pentyl-succinamide, or N4,N4-methoxymethyl-N1-(1-benzyl-2-(2-hydroxymethyl-pyrrolidin-1-yl)-2-oxo-ethyl-2-pentyl-succinamide.

4. A pharmaceutical composition, comprising a therapeutically effective amount of the compound of claim 1 and a pharmaceutically acceptable carrier.

5. A method for asymmetrically synthesizing a chemical compound having the structure of claim 1, said structure further comprising (S,S,R)-(−)-actinonin, said method comprising the steps of:

a) forming an optionally O-protected $R^1$-1-carbonyl-C2-($R^2$)-methyleneamine from $R^1$ and an N-protected $R^2$-amino acid 2,5-dioxo-pyrrolidinyl ester and deprotecting said N-protected $R^2$-amino acid with a suitable agent comprising trifluoroacetic acid;

b) forming an $R^3$-carbonyl-oxazolidone from 4-isopropyl-oxazolidin-2-one and $R^3$-carbonyl chloride;

c) treating a solution of 4-(S)-isopropyl-oxazolidin-2-one with a solution of a base comprising n-butyl lithium in hexanes and adding an $R^3$-carbonyl chloride thereby forming an $R^3$-carbonyl oxazolidinone;

d) treating a solution of the $R^3$-carbonyl oxazolidinone sequentially with a base comprising lithium diisopropylamide and with a bromo-$R^4$ acid-tert-butyl ester thereby forming an oxazolidine-$R^3$-carbonyl-$R^4$-acid tert-butyl ester;

e) treating a mixture of the an oxazolidine-$R^3$-carbonyl-$R^4$-acid tert-butyl ester in tetrahydrofuran and water sequentially with hydrogen peroxide in water and with lithium hydroxide in water thereby forming a C2($R^3$)-$R^4$-dicarboxylic acid tert-butyl ester;

f) treating a mixture of the C2($R^3$)-$R^4$-dicarboxylic acid 4-tert-butyl ester and hydroxysuccinimide in a solvent comprising dioxane or dimethylformamide with an imide comprising dicyclohexylcarbodiimide thereby forming an C2($R^3$)-$R^4$-dicarboxylic acid tert-butyl ester-(2,5-dioxo-pyrrolidin-1-yl) ester.

g) treating a solution of said optionally O-protected $R^1$-1-carbonyl-2-($R^2$)-methyleneamine in a solvent comprising tetrahydrofuran sequentially with triethylamine and with the C2($R^3$)-$R^4$-dicarboxylic acid tert-butyl ester-(2,5-dioxo-pyrrolidin-1-yl) ester thereby forming an optionally O-protected $R^1$-1-carbonyl-2-($R^2$)-carbamoyl-methylene($R^3$)-$R^4$-carboxylic acid tert-butyl ester;

h) treating a solution of said optionally O-protected $R^1$-1-carbonyl-C2($R^2$)-carbamoyl-methylene($R^3$)-$R^4$-carboxylic acid tert-butyl ester in a solvent comprising methylene chloride with trifluoroacetic acid thereby forming an optionally O-protected $R^1$-1-carbonyl-C2($R^2$)-carbamoyl-methylene($R^3$)-$R^4$-carboxylic acid;

i) treating said optionally O-protected $R^1$-1-carbonyl-2-($R^2$)-carbamoyl-methylene($R^3$)-$R^4$-carboxylic acid and hydroxysuccinamide with an imide comprising dicyclohexylcarbodiimide thereby forming a optionally O-protected $R^1$-1-carbonyl-C2($R^2$)-carbamoyl-methylene($R^3$)-$R^4$-carboxylic acid 2,5-dioxo-pyrrolidin-1-yl ester;

j) treating a suspension of $R^5$ or the chloride thereof, said $R^5$ optionally O-protected, in a solvent comprising dimethylformamide sequentially with triethylamine and with a solution of said O-protected $R^1$-1-carbonyl-C2($R^2$)-carbamoyl-methylene($R^3$)-$R^4$-carboxylic acid 2,5-dioxo-pyrrolidin-1-yl ester in a solvent comprising dimethylformamide thereby forming an $R^1$-1-carbonyl-C2($R^2$)-carbamoyl-methylene($R^3$)-$R^4$-carbonyl-$R^5$, said $R^1$ and $R^5$ independently optionally O-protected; and k) hydrogenating said $R^1$ and $R^5$, said $R^1$ and $R^5$ independently comprising an O-protecting group, with hydrogen gas and a catalyst comprising palladium hydroxide in activated carbon wherein (S,S,R)-(−)-actinonin or said chemical compound of claim 1 is thereby formed.

6. The method of claim 5, wherein:

$R^1$ is 2-hydroxymethyl-pyrrolidine, 2-methylpyrrolidine, 2-methylamine-pyrrolidine, methyl-2-pyrrolidine carboxylate, or 2-hydroxycarbamoyl;

$R^2$ is methyl, benzyl, 4-hydroxybenzyl, methylethyl, 2-methyl propyl, 3-methyl-indolyl;

$R^3$ is methyl or pentyl;

$R^4$ is methylene; and $R^5$ is $NH_2$, OH, NHOH, $NHOCH_3$, $N(CH_3)OH$, $N(CH_3)OCH_3$, $NHCH_2CH_3$, $NH(CH_2CH_3)$, $NHCH_2(2,4-(OCH3)_2Ph$, $NHCH_2(4-NO_2)Ph$, $NHN(CH_3)_2$, proline, 2-hydroxymethyl pyrrolidine. piperidine or 1-methyl-piperazine.

7. The method of claim 6, wherein when:

$R^1$ is 2-hydroxymethyl-pyrrolidine;

$R^2$ is benzyl;

$R^3$ is pentyl;

$R^4$ is methylene; and $R^5$ is $NHOCH_3$, $N(CH_3)OCH_3$, $NHCH_2CH_3$, $NH(CH_2CH_3)_2$, $NHCH_2(2,4-(OCH3)_2Ph$, $NHCH_2(4-NO_2)Ph$, $NHN(CH_3)_2$, piperidine, or 1-methyl-piperazine;

said chemical compositions are optionally synthesized from said C2($R^3$)-$R^4$-dicarboxylic acid tert-butyl ester-(2,5-dioxo-pyrrolidin-1-yl) ester comprising 2-pentylsuccinic acid 4-tert-butyl ester 4-(2,5-dioxo-pyrrolidin-1-yl) ester by a method comprising the steps of:

a) treating a solution of L-phenylalanine in a solvent comprising dimethylformamide sequentially with triethylamine and with the 2-pentylsuccinic acid 4-tert-butyl ester 4-(2,5-dioxo-pyrrolidin-1-yl) ester thereby forming an 3-(1-Carboxy-2-phenyl-ethylcarbamoyl)-octanoic acid tert-butyl ester;

b) coupling 2-hydroxymethyl pyrrolidine to 3-(1-Carboxy-2-phenyl-ethylcarbamoyl)-octanoic acid tert-butyl ester in a solvent comprising methylene chloride and in the presence of EDC and HOTS thereby forming 3-[1-(2-hydroxymethyl-pyrrolidin-1-yl)-2-benzylcarbamoyl]-octanoic acid 4-tert-butyl ester;

c) treating a solution of said 3-[1-(2-hydroxymethyl-pyrrolidin-1-yl)-2-benzylcarbamoyl]-octanoic acid 4-tert-butyl ester in a solvent comprising methylene chloride with trifluoroacetic acid thereby forming 3-[1-(2-hydroxymethyl-pyrrolidin-1-yl)-2-benzylcarbamoyl]-octanoic acid; and d) treating a suspension of $R^5$ in a solvent comprising methylene chloride and in the presence of EDC and HOBT with a solution of 3-[1-(2-hydroxymethyl-pyrrolidin-1-yl)-2-benzylcarbamoyl]-octanoic acid in methylene chloride to form N4($R^5$)-N1-[1-benzyl-2(2-hydroxymethyl-pyrrolidin-1-yl)-2-oxo-ethyl]-2-pentyl-succinamide.

8. The method of claim 5, wherein $R^1$ is 2-methyl pyrrolidine, 2-hydroxymethyl pyrrolidine or 2-hydroxycarbamoyl pyrrolidine; and $R^2$ is methyl, $CH_2CH_3$, $(CH_2)_2CH_3$, $C(CH_3)_3$;

$R^3$ is $R^2$ or $C_{4-7}$alkylene$CH_3$;

$R^4$ is methylene; and $R^5$ is hydroxyamine;

said method comprising the steps of:

a) coupling an O-protected methoxypyrrolidine or a derivative thereof with an N-protected amino acid 2,5-dioxo-(pyrrolidinyl ester thereby forming an N, O-protected methylpyrrolidine-1-carbonyl-2-methylamine or a derivative thereof;

b) deprotecting the N-protecting group with a deprotecting agent comprising trifluoracetic acid thereby forming a pyrrolidine-1-carbonyl-2-methylamine or a derivative thereof;

c) treating a solution of 4-(S)-isopropyl-oxazolidin-2-one with a solution of a base comprising n-butyl lithium in hexanes and adding an alkynoyl chloride thereby forming an alkynoyloxazolidinone;

d) treating a solution of the alkynoyloxazolidinone sequentially with a base comprising lithium diisopropylamide and with bromoacetic acid tert-butyl ester thereby forming a n oxazolidine-carbonyl-alkynoic acid tert-butyl ester;

e) treating a mixture of the oxazolidine-carbonyl-alkynoic acid tert-butyl ester in tetrahydrofuran and water sequentially with hydrogen peroxide in water and with lithium hydroxide in water thereby forming an alkylsuccinic acid 4-tert-butyl ester;

f) treating a mixture of the alkylsuccinic acid 4-tert-butyl ester and hydroxysuccinimide in a solvent comprising dioxane or dimethylformamide with an imide comprising dicyclohexylcarbodiimide thereby forming an alkylsuccinic acid 4-tert-butyl ester 4-(2, 5-dioxo-pyrrolidin-1-yl) ester;

g) treating a solution of the pyrrolidine-1-carbonyl-2-methylamine or the derivative thereof in a solvent comprising tetrahydrofuran sequentially with triethylamine and with the alkylsuccinic acid 4-tert-butyl ester 4-(2,5-dioxo-pyrrolidin-1-yl) ester thereby forming a pyrrolidine-1-carbonyl-2-methylalkyl-carbamoyl-alkynoic acid tert-butyl ester or a derivative thereof;

h) treating a solution of the pyrrolidine-1-carbonyl-2-methylalkyl-carbamoyl-alkynoic acid tert-butyl ester or the derivative thereof in a solvent comprising methylene with trifluoroacetic acid thereby forming a pyrrolidine-1-carbonyl-2-methyl-alkylcarbamoyl-alkynoic acid or a derivative thereof;

i) treating the pyrrolidine-1-carbonyl-2-methyl-alkylcarbamoyl-alkynoic acid or the derivative thereof and hydroxysucinamide with an imide comprising dicyclohexylcarbodiimide thereby forming a pyrrolidine-1-carbonyl-2-methyl-alkylcarbamoyl-alkynoic acid or a derivative thereof;

j) treating a suspension of O-benzylhydroxyamine hydrochloride in a solvent comprising dimethylformamide sequentially with triethylamine and with a solution of the pyrrolidine 1-carbonyl-2-methylalkylcarbamoyl-alkynoic acid 2,5-dioxo pyrrolidin-1-yl ester or the derivative thereof in a solvent comprising dimethylformamide thereby forming N4-benzyloxy-N1-(1-(pyrrolidine-1-carbonyl)-2-methylalkyl)-2-alkyl-succinamide or a derivative thereof; and k) hydrogenating N4-benzyloxy-N1-(1-(pyrrolidine-1-carbonyl)-2-methylalkyl)-2-alkyl-succinamide or the derivative thereof with hydrogen gas and a catalyst comprising palladium hydroxide in activated carbon.

9. The method of claim 8, wherein said chemical compound is (S,S,R)-(−)-actinonin, wherein $R^1$ is 2-hydroxymethyl pyrrolidine; $R^2$ is methylethyl; $R^3$ is pentyl; $R^4$ is methylene; and $R^5$ is hydroxyamine; said method comprising the steps of:

a) treating a solution of 4-(S)-isopropyl-oxazolidin-2-one in tetrahydrofuran at −78° C. with a solution of n-butyl lithium in hexanes;

b) adding heptanoyl chloride 3 thereby forming 3-heptanoyl-4-(S)-isopropyl-oxazolidin-2-one;

c) treating a solution of 3-heptanoyl-4-(S)-isopropyl-oxazolidin-2-one in tetrahydrofuran sequentially with lithium diisopropylamide and bromoacetic acid tert-butyl ester thereby forming 3-(4-(S)-isopropyl-2-oxo-oxazolidine-3-(S)-carbonyl) octanoic acid tert-butyl ester;

d) treating a mixture of 3-(4-(S)-isopropyl-2-oxo-oxazolidine-3-(S)-carbonyl)octanoic acid tert-butyl ester in THF and water sequentially with hydrogen peroxide in water and lithium hydroxide in water at 0° C. thereby forming 2-(R)-pentylsuccinic acid 4-tert-butyl ester;

e) mixing 2-(R)-pentylsuccinic acid 4-tert-butyl ester and hydroxysuccinimide in dimethylformamide or dioxane and treating the mixture with dicyclohexylcarbodiimide thereby forming 2-(R)-pentyl succinic acid 4-tert-butyl ester 4-(2,5-dioxo-pyrrolidin-1-yl) ester;

f) treating a solution of 2-(S)-benzyloxymethylpyrrolidine in tetrahydrofuran sequentially with triethylamine and a solution of 2-tert-butoxy carbonylamino-3-methylbutyric acid 2,5-dioxo-pyrrolidin-1-yl in tetrahydrofuran thereby forming (1-(2-benzyloxymethyl-pyrrolidine-1-carbonyl)-2-methyl-propyl)-carbamic acid tert-butyl ester;

g) dissolving (1-(2-benzyloxymethyl-pyrrolidine-1-carbonyl)-2-methyl-propyl)-carbamic acid tert-butyl ester in methylene and treating the solution with trifluoroacetic acid thereby forming 2-amino-1-(2-benzyloxymethylpyrrolidin-1-yl)-3-methyl butan-1-one;

h) treating 2-amino-1-(2-benzyloxymethylpyrrolidin-1-yl)-3-methylbutan-1-one in dimethylformamide sequentially with triethylamine and a solution of 2-(R)-pentylsuccinic acid 4-tert-butyl ester 4-(2,5-dioxo-pyrrolidin-1-yl) ester in dimethylformamide thereby forming 3-(1-(2-(S)-benzyloxymethylpyrrolidine-1-carbonyl)-2-(S)-methyl propyl-carbamoyl)-octanoic acid tert-butyl ester;

i) treating 3-(1-(2-(S)-benzyloxymethylpyrrolidine-1-carbonyl)-2-(S)-methyl propyl-carbamoyl)-octanoic acid tert-butyl ester in dichloromethane with trifluoroacetic acid thereby forming 3-(1-(2-benzyloxymethyl-pyrrolidine-1-carbonyl)-2-methyl-propyl carbamoyl)-octanoic acid;

j) treating a solution of 3-(1-(2-benzyloxymethyl-pyrrolidine-1-carbonyl)-2-methyl-propylcarbamoyl)-octanoic acid and hydroxysuccinamide with dicyclohexylcarbodiimide thereby forming 3-(1-(2-benzyloxymethyl-pyrrolidine-1-carbonyl)-2-methylpropyl carbamoyl)-octanoic acid 2,5-dioxo-pyrrolidin-1-yl ester;

k) treating a suspension of O-benzylhydroxyamine hydrochloride in dimethylformamide sequentially with triethylamine and a solution of 3-(1-(2-benzyloxymethyl-pyrrolidine-1-carbonyl)-2-methylpropylcarbamoyl)-octanoic acid 2,5-dioxo-pyrrolidin-1-yl ester in dimethylformamide thereby forming N4-benzyloxy-N1-(1-(2-benzyloxymethyl-pyrrolidine-1-carbonyl)-2-methyl-propyl)-2-pentyl-succinamide; and l) hydrogenating N4-benzyloxy-N1-(1-(2-benzyloxy methyl-pyrrolidine-1-carbonyl)-2-methyl-propyl)-2-pentyl-succinamide with hydrogen gas and palladium hydroxide in activated carbon wherein (S,S,R)-(–)-actinonin is thereby formed.

10. A method for the treatment of a neoplastic disease comprising the step of administering to an individual in need of such treatment a pharmacologically effective dose of the chemical compound of claim 1.

11. The method of claim 10, wherein said chemical compound is N4-hydroxy-N1-(1-(2-hydroxymethyl-pyrrolidine-1-carbonyl)-3-methyl-butyl)-2-pentyl-succinamide, N1-(1-(2-methyl-pyrrolidine-1-carbonyl)-2-methyl-propyl)-2-pentyl-succinamide, N1-(1-benzyl-2-(2-hydroxymethyl-pyrrolidin-1-yl)-2-oxo-ethyl)-N4-hydroxy-2-pentyl-succinamide, N4-hydroxy-N1-(1-(2-hydroxymethyl-pyrrolidine-1-carbonyl)-2-methyl-propyl)-2-methyl-succinamide, N4-hydroxy-N1-(1-benzyl-2-(2-methyl-pyrrolidin-1-yl)-2-oxo-ethyl-2-pentyl-succinamide, or N4-hydroxy-N1-(1-(methyl-2-carboxy-pyrrolidine-1-carbonyl)-2-methyl-propyl)-2-pentyl-succinamide.

12. The method of claim 10, wherein said individual is a human or an animal.

13. The method of claim 10, wherein said neoplastic disease is selected form the group consisting of human ovarian carcinoma, prostate carcinoma, mammary carcinoma, head and neck squamous cell carcinoma, non-small-cell-lung-cancer adenocarcinoma, non-small-cell-lung-cancer squamous cells, and acute myelogenous leukemia.

14. A method of inhibiting the growth of a tumor cell in vitro comprising the step of contacting said cell with a pharmacologically effective dose of the chemical composition of claim 1.

15. The method of claim 14, wherein said chemical compound is N4-hydroxy-N1-(1-(2-hydroxymethyl-pyrrolidine-1-carbonyl)-3-methyl-butyl)-2-pentyl-succinamide, N1-(1-(2-methyl-pyrrolidine-1-carbonyl)-2-methyl-propyl)-2-pentyl-succinamide, N1-(1-benzyl-2-(2-hydroxymethyl-pyrrolidin-1-yl)-2-oxo-ethyl)-N4-hydroxy-2-pentyl-succinamide, N4-hydroxy-N1-(1-(2-hydroxymethyl-pyrrolidine-1-carbonyl)-2-methyl-propyl)-2-methyl-succinamide, N4-hydroxy-N1-(1-benzyl-2-(2-methyl-pyrrolidin-1-yl)-2-oxo-ethyl-2-pentyl-succinamide, or N4-hydroxy-N1-(1-(methyl-2-carboxy-pyrrolidine-1-carbonyl)-2-methyl-propyl)-2-pentyl-succinamide.

16. The method of claim 14, wherein said tumor cell is selected from the group consisting of human ovarian cancer cells, prostate cancer cells, mammary cancer cells, head and neck squamous cancer cells, non-small-cell-lung-cancer cells, adenocarcinoma cells, non-small-cell-lung-cancer squamous cells, and acute myelogenous leukemic cells.

* * * * *